United States Patent
Arepally et al.

(10) Patent No.: US 11,338,117 B2
(45) Date of Patent: May 24, 2022

(54) IMPLANTABLE DUAL PATHWAY THERAPEUTIC AGENT DELIVERY PORT

(71) Applicant: TriSalus Life Sciences, Inc., Westminster, CO (US)

(72) Inventors: Aravind Arepally, Atlanta, GA (US); James E. Chomas, Denver, CO (US); Patrick Charles McCain, Denver, CO (US); David Benjamin Jaroch, Arvada, CO (US); Jennifer D. Lucky, Westminster, CO (US)

(73) Assignee: TriSalus Life Sciences, Inc., Westminster, CO (US)

( * ) Notice: Subject to any disclaimer, the term of this patent is extended or adjusted under 35 U.S.C. 154(b) by 275 days.

(21) Appl. No.: 16/405,605

(22) Filed: May 7, 2019

(65) Prior Publication Data

US 2020/0108239 A1 Apr. 9, 2020

Related U.S. Application Data

(60) Provisional application No. 62/742,573, filed on Oct. 8, 2018.

(51) Int. Cl.
  *A61M 39/02* (2006.01)
  *A61M 31/00* (2006.01)
  *A61M 25/00* (2006.01)
  *A61M 5/142* (2006.01)

(52) U.S. Cl.
  CPC ...... *A61M 31/002* (2013.01); *A61M 25/0026* (2013.01); *A61M 5/14276* (2013.01); *A61M 39/0208* (2013.01)

(58) Field of Classification Search
  CPC ...... A61M 2025/0037; A61M 39/0208; A61M 5/14276; A61M 2039/0211; A61M 2039/0235; A61M 2039/0238; A61M 39/04
  See application file for complete search history.

(56) References Cited

U.S. PATENT DOCUMENTS

| | | |
|---|---|---|
| 926,591 A | 6/1909 | Odquist |
| 4,261,341 A | 4/1981 | Hakim |
| 4,311,587 A | 1/1982 | Nose |
| 4,655,771 A | 4/1987 | Wallsten |
| 4,714,460 A | 12/1987 | Calderon |
| 4,738,740 A | 4/1988 | Pinchuk |

(Continued)

FOREIGN PATENT DOCUMENTS

| | | |
|---|---|---|
| CN | 101449987 A | 6/2009 |
| CN | 103260547 A | 8/2013 |

(Continued)

OTHER PUBLICATIONS

US 7,169,126 B2, 01/2007, Zadno-Azizi (withdrawn)

(Continued)

*Primary Examiner* — Deanna K Hall
(74) *Attorney, Agent, or Firm* — Gordon & Jacobson, P.C.

(57) ABSTRACT

A treatment system includes a dual lumen catheter system. The first lumen is open to systemic circulation. The second lumen is open to a target delivery location. In an embodiment, a pressure-control element is provided that includes an expanded configuration adapted to constrain delivery through the second lumen to the target delivery location. Methods for treating tissues and organs via vascular pathways are provided.

57 Claims, 11 Drawing Sheets

(56) References Cited

U.S. PATENT DOCUMENTS

| | | | |
|---|---|---|---|
| 4,800,016 | A | 1/1989 | Yang |
| 4,840,542 | A | 6/1989 | Abbott |
| 4,883,459 | A | 11/1989 | Calderon |
| 4,892,518 | A | 1/1990 | Cupp |
| 5,024,668 | A | 6/1991 | Peters et al. |
| 5,030,199 | A | 7/1991 | Barwick |
| 5,071,407 | A | 12/1991 | Termin |
| 5,084,015 | A | 1/1992 | Moriuchi |
| 5,234,425 | A | 8/1993 | Fogarty |
| 5,397,307 | A | 3/1995 | Goodin |
| 5,411,478 | A | 5/1995 | Stillabower |
| 5,419,763 | A | 5/1995 | Hildebrand |
| 5,484,399 | A | 1/1996 | DiResta et al. |
| 5,484,412 | A | 1/1996 | Pierpont |
| 5,496,277 | A | 3/1996 | Termin |
| 5,607,466 | A | 3/1997 | Imbert |
| 5,668,237 | A | 9/1997 | Popall |
| 5,688,237 | A | 11/1997 | Rozga |
| 5,725,571 | A | 3/1998 | Imbert |
| 5,755,687 | A | 5/1998 | Donlon |
| 5,755,769 | A | 5/1998 | Richard |
| 5,759,205 | A | 6/1998 | Valentini |
| 5,810,789 | A | 9/1998 | Powers |
| 5,836,905 | A | 11/1998 | Lemelson |
| 5,836,967 | A | 11/1998 | Schneider |
| 5,893,869 | A | 4/1999 | Barnhart |
| 5,895,399 | A | 4/1999 | Barbut |
| 5,897,567 | A | 4/1999 | Ressemann |
| 5,910,154 | A | 6/1999 | Tsugita |
| 5,911,734 | A | 6/1999 | Tsugita |
| 5,957,974 | A | 9/1999 | Thompson |
| 6,001,118 | A | 12/1999 | Daniel |
| 6,010,522 | A | 1/2000 | Barbut |
| 6,027,520 | A | 2/2000 | Tsugita |
| 6,042,598 | A | 3/2000 | Tsugita |
| 6,051,014 | A | 4/2000 | Jang |
| 6,059,745 | A | 5/2000 | Gelbfish |
| 6,152,946 | A | 11/2000 | Broome |
| 6,165,199 | A | 12/2000 | Barbut |
| 6,165,200 | A | 12/2000 | Tsugita |
| 6,168,579 | B1 | 1/2001 | Tsugita |
| 6,179,851 | B1 | 1/2001 | Barbut |
| 6,231,551 | B1 | 5/2001 | Barbut |
| 6,235,044 | B1 | 5/2001 | Root |
| 6,258,120 | B1 | 7/2001 | McKenzie |
| 6,306,074 | B1 | 10/2001 | Waksman |
| 6,306,163 | B1 | 10/2001 | Fitz |
| 6,309,399 | B1 | 10/2001 | Barbut |
| 6,361,545 | B1 | 3/2002 | Macoviak |
| 6,371,969 | B1 | 4/2002 | Tsugita |
| 6,371,971 | B1 | 4/2002 | Tsugita |
| 6,383,206 | B1 | 5/2002 | Gillick |
| 6,395,014 | B1 | 5/2002 | Macoviak |
| 6,416,495 | B1 | 7/2002 | Kriesel |
| 6,436,112 | B2 | 8/2002 | Wensel |
| 6,443,926 | B1 | 9/2002 | Kletschka |
| 6,478,783 | B1 | 11/2002 | Moorehead |
| 6,485,456 | B1 | 11/2002 | Kletschka |
| 6,485,502 | B2 | 11/2002 | Don Michael |
| 6,499,487 | B1 | 12/2002 | McKenzie |
| 6,500,203 | B1 | 12/2002 | Thompson |
| 6,520,183 | B2 | 2/2003 | Amar |
| 6,530,935 | B2 | 3/2003 | Wensel |
| 6,533,800 | B1 | 3/2003 | Barbut |
| 6,537,294 | B1 | 3/2003 | Boyle |
| 6,537,297 | B2 | 3/2003 | Tsugita |
| 6,540,722 | B1 | 4/2003 | Boyle |
| 6,551,303 | B1 | 4/2003 | Van Tassel |
| 6,565,552 | B1 | 5/2003 | Barbut |
| 6,569,146 | B1 | 5/2003 | Werner |
| 6,582,396 | B1 | 6/2003 | Parodi |
| 6,589,264 | B1 | 7/2003 | Barbut |
| 6,592,546 | B1 | 7/2003 | Barbut |
| 6,607,506 | B2 | 8/2003 | Kletschka |
| 6,620,148 | B1 | 9/2003 | Tsugita |
| 6,635,070 | B2 | 10/2003 | Leeflang |
| 6,641,553 | B1 | 11/2003 | Chee |
| 6,641,572 | B2 | 11/2003 | Cherkassky |
| 6,645,220 | B1 | 11/2003 | Huter |
| 6,645,222 | B1 | 11/2003 | Parodi |
| 6,645,223 | B2 | 11/2003 | Boyle |
| 6,652,555 | B1 | 11/2003 | VanTassel |
| 6,652,556 | B1 | 11/2003 | VanTassel |
| 6,656,351 | B2 | 12/2003 | Boyle |
| 6,673,090 | B2 | 1/2004 | Root |
| 6,676,682 | B1 | 1/2004 | Tsugita |
| 6,689,150 | B1 | 2/2004 | VanTassel |
| 6,692,508 | B2 | 2/2004 | Wensel |
| 6,692,509 | B2 | 2/2004 | Wensel |
| 6,692,513 | B2 | 2/2004 | Streeter |
| 6,695,813 | B1 | 2/2004 | Boyle |
| 6,695,858 | B1 | 2/2004 | Dubrul |
| 6,699,231 | B1 | 3/2004 | Sterman |
| 6,702,834 | B1 | 3/2004 | Boylan |
| 6,706,053 | B1 | 3/2004 | Boylan |
| 6,706,055 | B2 | 3/2004 | Douk |
| 6,730,108 | B2 | 5/2004 | VanTassel |
| 6,746,469 | B2 | 6/2004 | Mouw |
| 6,746,489 | B2 | 6/2004 | Dua |
| 6,802,317 | B2 | 10/2004 | Goebel |
| 6,818,006 | B2 | 11/2004 | Douk |
| 6,830,579 | B2 | 12/2004 | Barbut |
| 6,837,898 | B2 | 1/2005 | Boyle |
| 6,855,154 | B2 | 2/2005 | Abdel-Gawwad |
| 6,866,677 | B2 | 3/2005 | Douk |
| 6,887,258 | B2 | 5/2005 | Denison |
| 6,896,690 | B1 | 5/2005 | Lambrecht |
| 6,902,540 | B2 | 6/2005 | Dorros |
| 6,908,474 | B2 | 6/2005 | Hogendijk |
| 6,911,036 | B2 | 6/2005 | Douk |
| 6,936,060 | B2 | 8/2005 | Hogendijk |
| 6,939,362 | B2 | 9/2005 | Boyle |
| 6,964,670 | B1 | 11/2005 | Shah |
| 6,964,673 | B2 | 11/2005 | Tsugita |
| 6,974,469 | B2 | 12/2005 | Broome |
| 6,989,027 | B2 | 1/2006 | Allen |
| 6,997,898 | B2 | 2/2006 | Forman |
| 7,044,958 | B2 | 5/2006 | Douk |
| 7,044,966 | B2 | 5/2006 | Svanidze |
| 7,066,946 | B2 | 6/2006 | Douk |
| 7,101,396 | B2 | 9/2006 | Artof |
| 7,118,600 | B2 | 10/2006 | Dua |
| 7,162,303 | B2 | 1/2007 | Levin |
| 7,169,164 | B2 | 1/2007 | Borillo |
| 7,172,614 | B2 | 2/2007 | Boyle |
| 7,172,621 | B2 | 2/2007 | Theron |
| 7,214,237 | B2 | 5/2007 | Don Michael |
| 7,217,255 | B2 | 5/2007 | Boyle |
| 7,223,253 | B2 | 5/2007 | Hogendijk |
| 7,232,452 | B2 | 6/2007 | Adams |
| 7,232,453 | B2 | 6/2007 | Shimon |
| 7,241,304 | B2 | 7/2007 | Boyle |
| 7,250,041 | B2 | 7/2007 | Chiu |
| 7,252,675 | B2 | 8/2007 | Denison |
| 7,279,000 | B2 | 10/2007 | Cartier |
| 7,306,575 | B2 | 12/2007 | Barbut |
| 7,322,957 | B2 | 1/2008 | Kletschka |
| 7,326,226 | B2 | 2/2008 | Root |
| 7,331,973 | B2 | 2/2008 | Gesswein |
| 7,338,510 | B2 | 3/2008 | Boylan |
| 7,344,549 | B2 | 3/2008 | Boyle |
| 7,364,566 | B2 | 4/2008 | Elkins |
| 7,371,249 | B2 | 5/2008 | Douk |
| 7,425,215 | B2 | 9/2008 | Boyle |
| 7,503,904 | B2 | 3/2009 | Choi |
| 7,537,600 | B2 | 5/2009 | Eskuri |
| 7,544,202 | B2 | 6/2009 | Cartier |
| 7,572,272 | B2 | 8/2009 | Denison |
| 7,582,100 | B2 | 9/2009 | Johnson |
| 7,585,309 | B2 | 9/2009 | Larson |
| 7,591,832 | B2 | 9/2009 | Eversull |
| 7,604,650 | B2 | 10/2009 | Bergheim |
| 7,647,115 | B2 | 1/2010 | Levin |
| 7,653,438 | B2 | 1/2010 | Deem |

(56) References Cited

U.S. PATENT DOCUMENTS

| | | |
|---|---|---|
| 7,658,747 B2 | 2/2010 | Forde |
| 7,686,781 B2 | 3/2010 | Vinten-Johansen |
| 7,833,242 B2 | 11/2010 | Gilson |
| 7,842,084 B2 | 11/2010 | Bicer |
| 7,846,139 B2 | 12/2010 | Zinn |
| 7,853,333 B2 | 12/2010 | Demarais |
| 7,873,417 B2 | 1/2011 | Demarais |
| 7,922,691 B2 | 4/2011 | Kletchka |
| 7,935,075 B2 | 5/2011 | Tockman |
| 7,937,143 B2 | 5/2011 | Demarais |
| 7,938,799 B2 | 5/2011 | Epstein |
| 7,993,324 B2 | 8/2011 | Barbut |
| 8,162,879 B2 | 4/2012 | Hattangadi |
| 8,172,792 B2 | 5/2012 | Wang |
| 8,182,446 B2 | 5/2012 | Schaeffer |
| 8,200,312 B2 | 6/2012 | Degani |
| 8,251,948 B2 | 8/2012 | Goldman |
| 8,257,384 B2 | 9/2012 | Bates |
| 8,262,611 B2 | 9/2012 | Teesllink |
| 8,397,578 B2 | 3/2013 | Miesel |
| 8,409,166 B2 | 4/2013 | Wiener |
| 8,500,775 B2 | 8/2013 | Chomas |
| 8,696,698 B2 | 4/2014 | Chomas |
| 8,696,699 B2 | 4/2014 | Chomas |
| 8,821,476 B2 | 9/2014 | Agah |
| 8,852,207 B2 | 10/2014 | Simpson |
| 9,023,010 B2 | 5/2015 | Chiu |
| 9,061,117 B2 | 6/2015 | Roberts |
| 9,078,982 B2 | 7/2015 | Lane |
| 9,089,341 B2 | 7/2015 | Chomas |
| 9,126,016 B2 | 9/2015 | Chomas |
| 9,174,020 B2 | 11/2015 | Allen |
| 9,205,226 B2 | 12/2015 | Allen |
| 9,265,914 B2 | 2/2016 | Fulton, III |
| 9,364,358 B2 | 6/2016 | Cohen |
| 9,457,171 B2 | 10/2016 | Agah |
| 9,463,304 B2 | 10/2016 | Agah |
| 9,474,533 B2 | 10/2016 | Mathis |
| 9,539,081 B2 | 1/2017 | Chomas |
| 9,550,046 B1 | 1/2017 | Allen |
| 9,597,480 B2 | 3/2017 | Purdy |
| 9,604,037 B2 | 3/2017 | Fischer, Jr. |
| 9,770,319 B2 | 9/2017 | Pinchuk |
| 9,808,332 B2 | 11/2017 | Chomas |
| 9,844,383 B2 | 12/2017 | Allen |
| 9,913,959 B2 | 3/2018 | Purdy |
| 9,968,740 B2 | 5/2018 | Pinchuk |
| 10,092,742 B2 | 10/2018 | Genstler |
| 10,099,040 B2 | 10/2018 | Agah |
| 10,130,762 B2 | 11/2018 | Allen |
| 2001/0041862 A1 | 11/2001 | Glickman |
| 2002/0042593 A1 | 4/2002 | Mickley |
| 2002/0161390 A1 | 10/2002 | Mouw |
| 2002/0161394 A1 | 10/2002 | Macoviak |
| 2003/0097114 A1 | 5/2003 | Duriel |
| 2003/0125790 A1 | 7/2003 | Fastovsky |
| 2003/0187474 A1 | 10/2003 | Keegan |
| 2003/0212361 A1 | 11/2003 | Boyle |
| 2003/0233115 A1 | 12/2003 | Eversull |
| 2004/0054315 A1 | 3/2004 | Levin |
| 2004/0068288 A1 | 4/2004 | Palmer |
| 2004/0143185 A1 | 7/2004 | Zatezalo |
| 2004/0215142 A1 | 10/2004 | Matheis |
| 2004/0220511 A1 | 11/2004 | Scott |
| 2004/0220521 A1 | 11/2004 | Barbut |
| 2004/0220609 A1 | 11/2004 | Douk |
| 2004/0225354 A1 | 11/2004 | Allen |
| 2004/0256584 A1 | 12/2004 | Zimmerling |
| 2004/0260333 A1 | 12/2004 | Dubral |
| 2005/0004517 A1 | 1/2005 | Courtney |
| 2005/0010285 A1 | 1/2005 | Lambrecht |
| 2005/0015048 A1 | 1/2005 | Chiu |
| 2005/0015112 A1 | 1/2005 | Cohn |
| 2005/0119688 A1 | 6/2005 | Burgheim |
| 2005/0149112 A1 | 7/2005 | Barbut |
| 2005/0261759 A1 | 11/2005 | Lambrecht |
| 2006/0124140 A1 | 6/2006 | Forsell |
| 2006/0167537 A1 | 7/2006 | Larsson |
| 2006/0173490 A1 | 8/2006 | LaFontaine |
| 2006/0177478 A1 | 8/2006 | Humes |
| 2006/0264898 A1 | 11/2006 | Beasley |
| 2007/0106258 A1 | 5/2007 | Chiu |
| 2007/0106324 A1 | 5/2007 | Gamer |
| 2007/0179590 A1 | 8/2007 | Lu |
| 2007/0239135 A9 | 10/2007 | Barbut |
| 2008/0031740 A1 | 2/2008 | Miyazaki |
| 2008/0031962 A1 | 2/2008 | Boyan |
| 2008/0033341 A1 | 2/2008 | Grad |
| 2008/0039786 A1 | 2/2008 | Epstein |
| 2008/0097273 A1 | 4/2008 | Levin |
| 2008/0103523 A1 | 5/2008 | Chiu |
| 2008/0147007 A1 | 6/2008 | Freyman |
| 2009/0018498 A1 | 1/2009 | Chiu |
| 2009/0076409 A1 | 3/2009 | Wu |
| 2009/0088676 A1 | 4/2009 | Murata |
| 2009/0198321 A1 | 8/2009 | Sutermeister |
| 2009/0222035 A1 | 9/2009 | Schneiderman |
| 2009/0234266 A1 | 9/2009 | Solomon |
| 2009/0234283 A1 | 9/2009 | Burton |
| 2009/0264819 A1 | 10/2009 | Diethrich |
| 2010/0168785 A1 | 7/2010 | Parker |
| 2010/0331815 A1 | 12/2010 | Alt |
| 2011/0046542 A1 | 2/2011 | Evans |
| 2011/0130657 A1 | 6/2011 | Chomas |
| 2011/0137399 A1 | 6/2011 | Chomas |
| 2011/0218494 A1 | 9/2011 | Gerrans |
| 2011/0288529 A1 | 11/2011 | Fulton |
| 2011/0295114 A1 | 12/2011 | Agah |
| 2011/0295203 A1 | 12/2011 | Hayes |
| 2012/0116351 A1 | 5/2012 | Chomas |
| 2012/0259206 A1 | 10/2012 | Roberts |
| 2013/0079731 A1 | 3/2013 | Chomas |
| 2013/0116655 A1 | 5/2013 | Bacino |
| 2013/0226166 A1 | 8/2013 | Chomas |
| 2014/0066830 A1 | 3/2014 | Lad |
| 2014/0207178 A1 | 7/2014 | Chomas |
| 2014/0276135 A1 | 9/2014 | Agah |
| 2014/0276411 A1 | 9/2014 | Cowan |
| 2014/0364835 A1 | 12/2014 | Allen |
| 2014/0378951 A1 | 12/2014 | Dye |
| 2015/0272716 A1 | 10/2015 | Pinchuk |
| 2015/0306311 A1 | 10/2015 | Pinchuk |
| 2016/0015508 A1 | 1/2016 | Chomas |
| 2016/0015948 A1 | 1/2016 | Agah |
| 2016/0074633 A1 | 3/2016 | Schaffner |
| 2016/0082178 A1 | 3/2016 | Agah |
| 2016/0235942 A1 | 8/2016 | Alt |
| 2016/0235950 A1 | 8/2016 | Murata |
| 2016/0256626 A9 | 9/2016 | Chomas |
| 2016/0310148 A1 | 10/2016 | Allen |
| 2017/0000493 A1 | 1/2017 | Boehm, Jr. |
| 2017/0049946 A1 | 2/2017 | Kapur |
| 2017/0056629 A1 | 3/2017 | Agah |
| 2017/0157370 A1 | 6/2017 | Agah |
| 2017/0173309 A1 | 6/2017 | Fischer, Jr. |
| 2017/0189654 A1 | 7/2017 | Schwartz |
| 2017/0209666 A1 | 7/2017 | Quigley |
| 2017/0319820 A1 | 11/2017 | Johnson |
| 2017/0368306 A1 | 12/2017 | Tal |
| 2018/0055620 A1 | 1/2018 | Chomas |
| 2018/0116522 A1 | 5/2018 | Brenneman |
| 2018/0125502 A1 | 5/2018 | Allen |
| 2018/0250469 A1 | 9/2018 | Pinchuk |
| 2018/0263752 A1 | 9/2018 | Pinchuk |
| 2018/0289464 A1 | 10/2018 | Kassab |
| 2018/0333563 A1 | 11/2018 | Agah |
| 2019/0046157 A1 | 2/2019 | Unser |
| 2019/0083705 A1 | 3/2019 | Allen |
| 2020/0038586 A1 | 2/2020 | Chomas et al. |
| 2020/0078555 A1 | 3/2020 | Agah |
| 2020/0108239 A1 | 4/2020 | Arepally et al. |

(56) References Cited

U.S. PATENT DOCUMENTS

| | | | |
|---|---|---|---|
| 2020/0261695 | A1 | 8/2020 | Jaroch et al. |
| 2021/0338976 | A1 | 11/2021 | Jaroch et al. |

FOREIGN PATENT DOCUMENTS

| | | | |
|---|---|---|---|
| CN | 203107204 U | | 8/2013 |
| CN | 105007973 A | | 10/2015 |
| CN | 105208946 A | | 12/2015 |
| DE | 8910603 U1 | | 12/1989 |
| EP | 0416662 B1 | | 3/1991 |
| EP | 0533511 A1 | | 3/1993 |
| EP | 0554579 A1 | | 8/1993 |
| EP | 1226795 | | 7/2002 |
| EP | 1527740 | | 5/2005 |
| EP | 1743524 | | 1/2007 |
| EP | 1803423 | | 7/2007 |
| EP | 2359893 A1 | | 8/2011 |
| FR | 2652267 A1 | | 3/1991 |
| GB | 2020557 B | | 11/1979 |
| WO | 8905667 | | 6/1989 |
| WO | 199916382 | | 4/1999 |
| WO | 199944510 A1 | | 9/1999 |
| WO | 200141679 | | 6/2001 |
| WO | 200145592 | | 6/2001 |
| WO | 200149215 A2 | | 7/2001 |
| WO | 0197879 | | 12/2001 |
| WO | 2004043293 | | 5/2004 |
| WO | 2011068946 | | 6/2011 |
| WO | 2019140381 A1 | | 7/2019 |

OTHER PUBLICATIONS

Search Report and Written Opinion dated Jan. 6, 2020 of application No. PCT/US 19/54406.
Allogenic Chimeric Antigen Receptor-Modified Cells for Adoptive Cell Therapy of Cancer, Marcus, Assaf et al., Mar. 24, 2014, Expert Opinion of Biological Therapy, vol. 14, Issue 7.
A Study of the Geometrical and Mechanical Properties of a Self-Expandig Metallic Stent Theory and Experiment, Dr. Michael R. Jedwab, Claude O. Clerc, Journal of Applied Biomaterials, vol. 4, Issue 1, pp. 77-85, Spring 1993.
U.S. Appl. No. 61/266,068, filed Dec. 2, 2009, Chomas et al.
U.S. Appl. No. 61/382,290, filed Sep. 13, 2010, Chomas et al.
Cannulation of the Cardiac Lymphatic Sytem in Swine, Vazquez-Jiminez et al., European Journal of Cardio-thoracic Surgery 18 (2000) 223-232.
Catheter-Based Renal Sympathetic Denervation for Resistant Hypertension: a Multicentre Safety and Proof-of-Principle Cohort Study, Krum et al, The Lancet, 2009.
Development of Repeatable Microcatheter Access Port for Intra-arterial Therapy of Liver Cancer, Yasushi Fukuoka et al., Cardiovasc Intervent Radiol (2019) 42:298-303.
Embolization II, Scientific Session 11, JVIR, Mar. 27, 2012.
Embolization procedure lowers levels of "hunger hormone," leads to weight loss, EurekAlert Public Release, Mar. 7, 2013.
Estimation of Tumor Interstitial Fluid Pressure (TIFP) Noninvasively, Long Lian Liu et al., PLOS One | DOI:10.1371/journal.pone.0140892 Jul. 28, 2016.
Finite Element Stent Design, M. De Beule, R. Van Impe, P. Verdonck, B. Verhegghe, Computer Methods in Biomechanics and Biomedical Engineering, 2005.
First-In-Man Study of Left Gastric Artery Embolization for Weight Loss, Nicholas Kipshidze et al., ACC.13, E2056, UACC Mar. 12, 2013, vol. 61, Issue 10.
Fusion Drug Delivery System-Novel Catheter/Stent Design for Targeted Drug Delivery, Gerschwind & Barnett, Non-Published US provisional patent application filed Sep. 17, 2007.
International Search Report and Written Opinion of Application No. PCT/US16/23723 dated Sep. 2, 2016.
International Search Report and Written Opinion of Application No. PCT/US19/13482 dated Jun. 10, 2019.
International Search Report of PCT/US18/22171 dated Aug. 3, 2018.
Left Gastric Embolization Leads to Weight Loss, Bariatriac News, Owen Haskins, Dec. 4, 2013.
Long-Term Catheterization of the Intestinal Lymph Trunk and Collection of Lymph in Neonatal Pigs, Richard R. Uwiera et al., Journal of Visualized Experiments, Mar. 2016, 109, e53457.
Lymphaniography to Treat Postoperative Lymphatic Leakage: A Technical Review, Edward Wolfgang Lee, et al., Korean Journal of Radiology 15(6), Nov./Dec. 2014.
Radiologic Placement of Side-hole Catheter with Tip Fixation for Hepatic Arterial Infusion Chemotherapy, Toshihiro Tanaka et al., J Vasc Interv Radiol 2003: 14:63-68.
Renal Denervation as a Therapeutic Approach for Hypertension: Novel Implications for an Old Concept, Schlaich et al., Hypertension, Journal of the American Heart Association, 2009, 54:1195-1201.
Renal Sympathetic-Nerve Ablation for Uncontrolled Hypertension, Schlaich et al., The New England Journal of Medicine, 2009, pp. 932-934, Aug. 27, 2009.
RenovoCath(tm) RC120 The Future of Targeted Delivery, RenovoRx Inc., web brochure downloaded from Internet on Feb. 2, 2015.
Superselective Retrograde Lymphatic Duct Embolization for Management of Postoperataive Lymphatic Leak, Bulent Arslan et al., Diagn Interv Radiol 2017; 23:379-380.
EP Search Report and Written Opinion of Application No. EP19739019 dated Sep. 17, 2021.
Chinese Office Action and Search Report dated Jan. 10, 2022 of Application No. 201980016342.3.
U.S. Appl. No. 15/871,326, filed Jan. 15, 2018, Arepally et al.
U.S. Appl. No. 17/375,779, filed Jul. 14, 2021, Arepally et al.
U.S. Appl. No. 17/671,296, filed Feb. 14, 2022, Arepally et al.

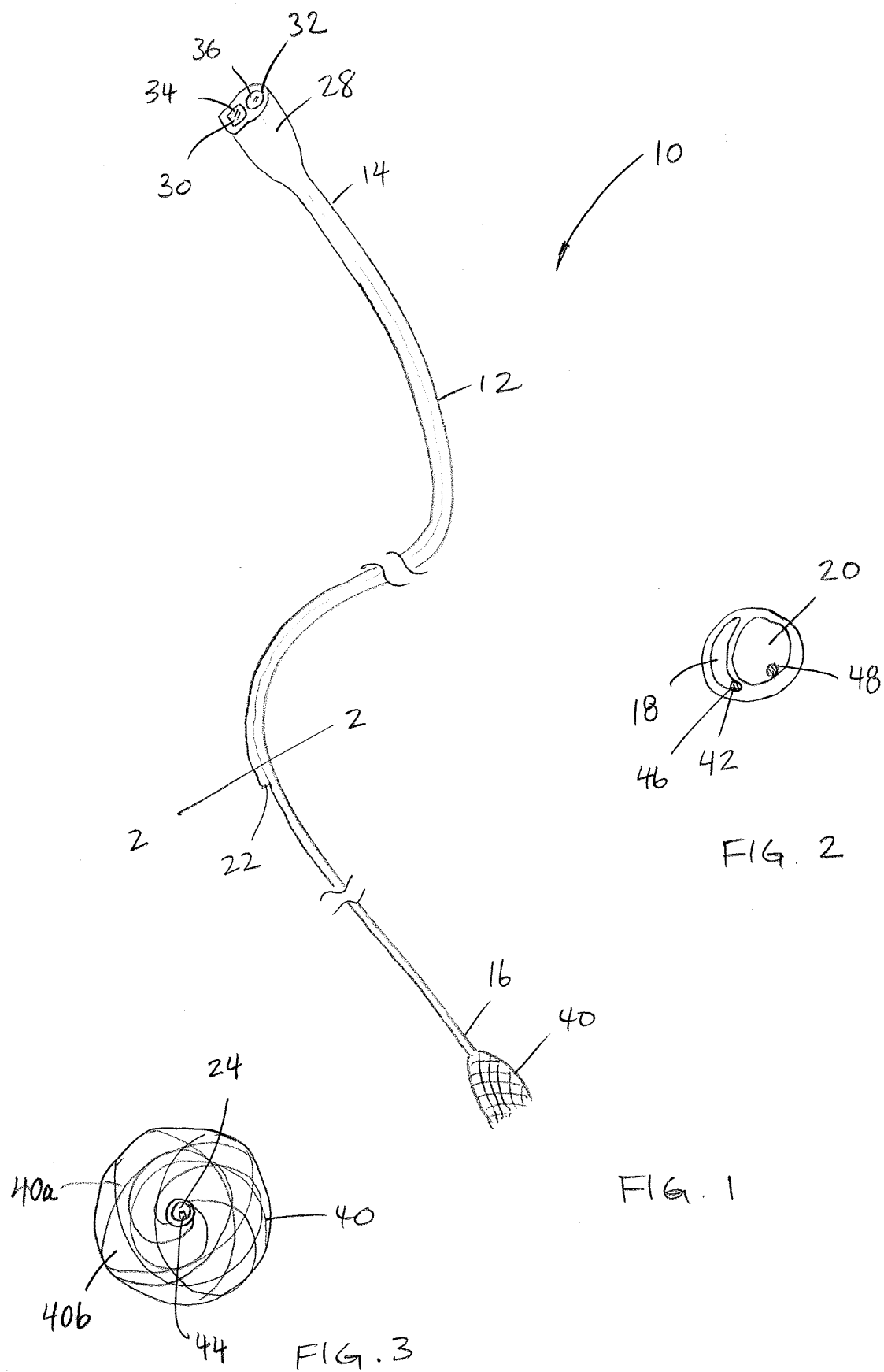

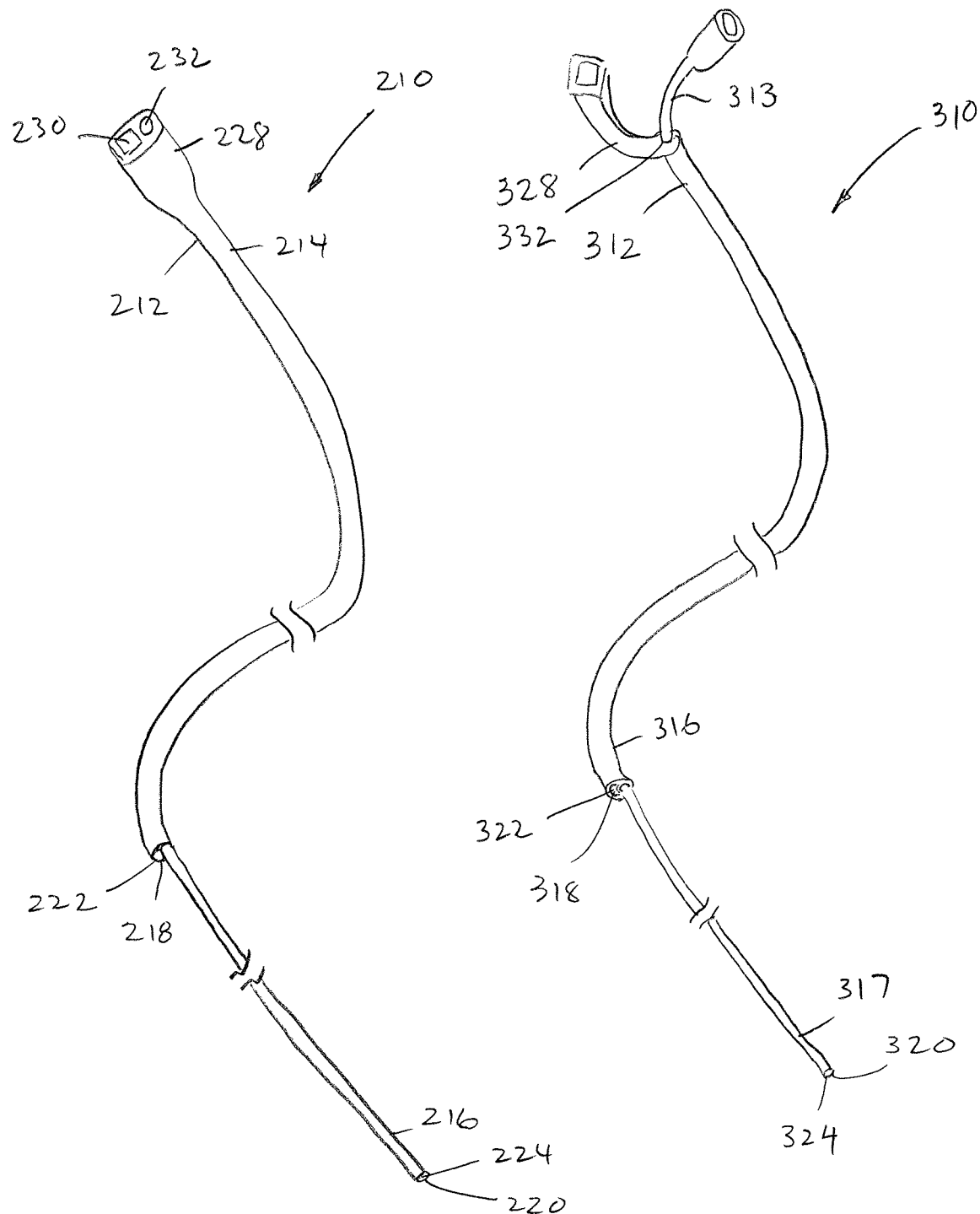

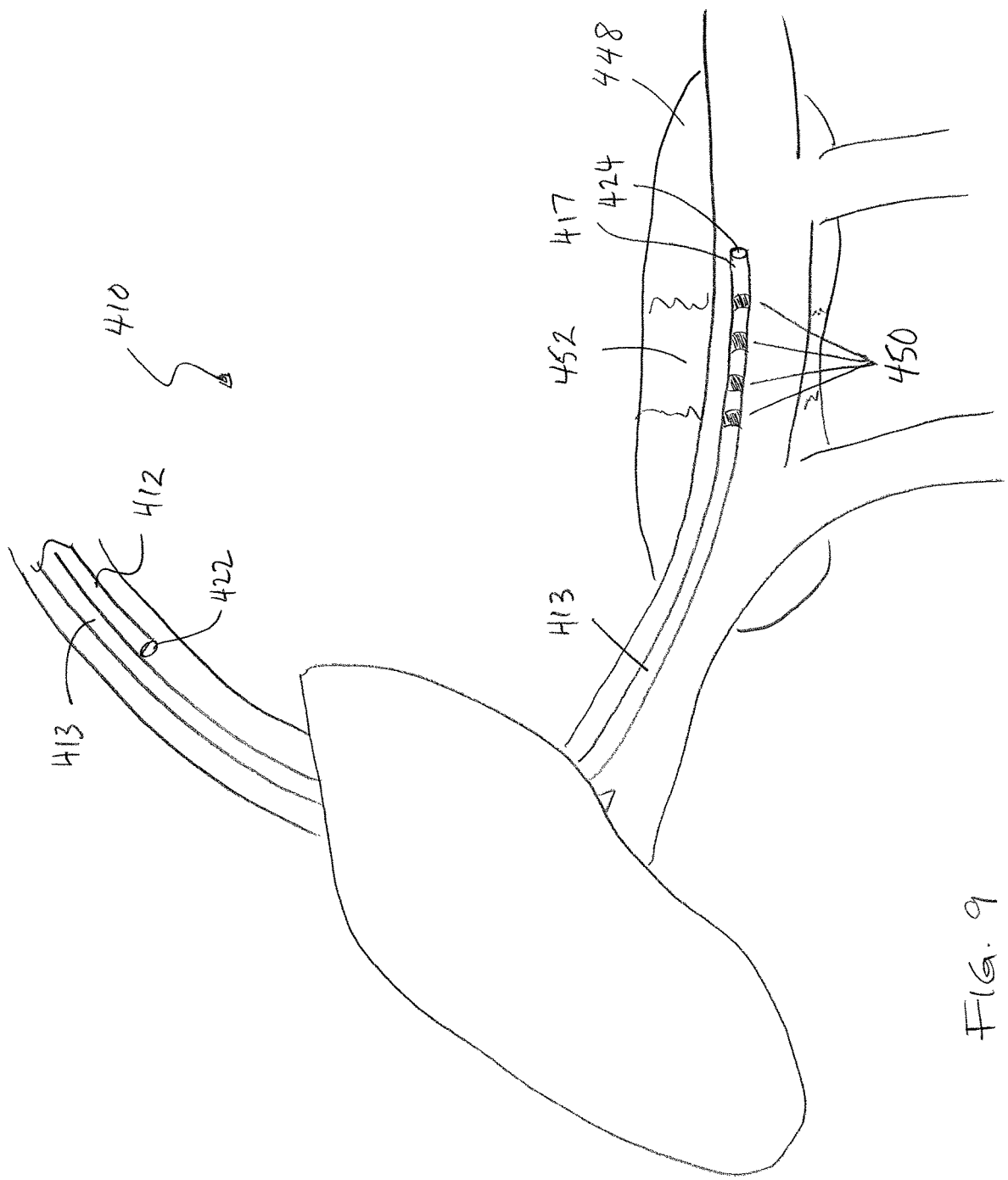

IMPLANTABLE DUAL PATHWAY THERAPEUTIC AGENT DELIVERY PORT

CROSS-REFERENCE TO RELATED APPLICATIONS

This application claims benefit to U.S. Provisional App. 62/742,573, filed Oct. 8, 2018, which is hereby incorporated by reference herein in its entirety.

This application is also related to U.S. Ser. No. 15/871,326, filed Jan. 15, 2018, which is a continuation-in-part of U.S. Ser. No. 15/703,951, filed Sep. 13, 2017, which claims benefit to U.S. Provisional Application Ser. No. 62/396,622, filed Sep. 19, 2016, which are hereby incorporated by reference herein in their entireties.

BACKGROUND OF THE INVENTION

1. Field of the Invention

The medical devices and methods described herein relate generally to devices and methods for delivery of a treatment through a vessel to a target tissue for the treatment of a disease or other medical condition.

2. State of the Art

For some diseases, systemic treatments are used to treat the patient. The effectiveness of some such systemic treatments can vary due at least in part to the treatment agent (e.g., a radio-embolization agent, a biologic agent and/or other treatment formulation) not reaching target tissue. For example, in the treatment of some diseases such as pancreatic cancer and/or diabetes, it may be desirable to deliver biological cells to the pancreas where efficient and safe engraftment can be achieved, and especially to the pancreatic tail, for example, where a large number of the endogenous islet cells reside. Some systemic treatments for diabetes, which affects the body's ability to produce and/or regulate insulin, have attempted to transplant insulin producing beta cells into pancreatic tissue, however, with limited success due to a lack of supply and a long-term need for immunosuppression. In other forms of treatment for diabetes, transplantation of autologous stem cells (mesenchymal, bone marrow, and others) can increase and/or replace the supply of insulin, especially in Type II diabetes where autoimmune reaction against these cells appears limited. In such treatments, various methods have been used such as, for example, transplanting the cells surgically in the sub capsular space in the kidney, the liver, and nonselective systemic injection both intravenously and intra-arterially, with the hope of "homing" these cells to the pancreatic tissue to allow engraftment, however, a best mode of transplantation has yet to established.

In some instances, a treatment can include transplanting such cells into the pancreas itself. For example, one treatment has included sub-selective endovascular injection of these cells into the arterial supply of the pancreatic tissue. Such an approach, however, is subject to variation in the number of cells actually introduced to the pancreas (versus other organs in the same vascular bed including the spleen, the liver, and/or the stomach). Furthermore, inadvertent exposure of other non-target organs to such cells can result in health risks for the patient.

Treatments for pancreatic cancer can be similarly ineffective. For example, pancreatic cancer is considered an almost chemoresistant tumor. The ineffective result of systemic chemotherapy is at least in part due to an insufficient drug concentration within the tumor because of dose-limited toxicity in bone marrow and epithelial tissue. Since systemic chemotherapy is limited in its effectiveness, treatments beyond systemic chemotherapy can be desirable for advanced pancreatic cancer patients. For example, one such treatment can include local intra-arterial delivery of chemotherapy. Intra-arterial infusion allows higher drug concentration to reach the tumor. Furthermore, intra-arterial chemotherapy can also take advantage of the first pass effect of chemotherapeutics, generating higher-level drug concentrations at the tumor cell membrane and therefore, enhancing cellular drug uptake as compared to intravenous infusion. Lastly, local delivery can reduce systemic side effects.

Portal venous pressure is the blood pressure in the hepatic portal vein, and is normally between 5-10 mmHg. Raised portal venous pressure is termed portal hypertension, and has numerous sequalae such as ascites, hepatic encephalopathy and variceal bleeding. Systemic venous pressure is the blood pressure typically measured in the hepatic vein, superior vena cava, inferior vena cava, or right atrium; i.e., as close as reasonable to the heart. The porto-systemic gradient is a measurement of the pressure gradient between the portal vein and systemic venous pressure. When the porto-systemic gradient exceeds 5 mmHg a condition of portal hypertension is defined, and if the gradient exceeds 10 mmHg a condition of clinically signal portal hypertension is defined. This gradient is significant monitor because at a gradient above 12 mmHg, variceal hemorrhaging may occur.

Whereas normal portal vein blood flow is at 1 to 1.5 liters per minute, an increased gradient is indicative of increased resistance to portal blood flow which causes formation of portosystemic collateral vessels that divert portal blood flow to the systemic circulation, this bypassing the liver. While not widely performed, such gradient assessment in persons with chronic liver disease is recommended to monitor a response and potential effectiveness of treatment.

Intra-vascular chemotherapy treatment to an organ is usually administered through a small catheter placed in a blood vessel in close fluid communication with the organ. An issue in catheter localization is the redundant nature of blood supply to the pancreas overlapping adjacent organs. Furthermore, the small size and anatomical variability of the branches of the hepatic and splenic arteries to the pancreas precludes reproducible cannulization via interventional techniques. Delivering the therapy to the correct location requires knowledge of the patient's arterial anatomy, preferably obtained through visualization techniques in advance of therapeutic delivery of the treatment.

Even then, standard catheters permit only limited control of the infused treatment. The treatment will flow from an area of high pressure to an area of lower pressure. Given the cyclic pressure operating on the blood as the heart beats, the treatment can reflux into healthy tissues where it will do harm, rather than good.

In order to alleviate certain of these issues, co-owned U.S. Pat. No. 8,696,698 to Chomas describes a pressure-controlled therapeutic delivery device in the form of a microvalve mounted at the distal end of catheter. The microvalve dynamically expands and contracts within a blood vessel in relation to the surrounding blood pressure. A treatment can be infused through the catheter under significant pressure. When the treatment agent is infused, the pressure in the vessel downstream (distal) of the treatment is always higher than that upstream (proximal) of the treatment, causing the microvalve to automatically and dynamically open and block reflux of the agent.

US Pub. No. 2016/0082178 to Agah discloses a device and method for isolating and visualizing feeder vessels using an endovascular approach. The device includes an outer catheter and an inner catheter longitudinally displaceable in a telescoping arrangement. An occlusive element is coupled to each catheter. The outer catheter includes side openings, and an agent can be infused through the outer catheter and out of the side openings between the two occlusive elements. In use, the device is advanced to the portal vein, and the catheters are displaced to locate the occluders on opposing sides of feeder vessels. The occluders are then expanded to isolate a region of the portal vein containing the feeder vessels, thereby causing cessation of blood flow within the isolated region. Then a contrast agent is injected through the outer catheter, out the side openings, and into the portal vein, where it travels only within the isolated region of the portal vein and off to the feeder vessels of the portal vein to visualize the vessels. A similar subsequent step can be performed to inject a therapeutic agent into the portal vein and feeder vessels.

This system has several disadvantages. As the portal vein does not have significant tubular strength and can expand when subject to the increased pressure of the injected therapeutic agent, the agent may flow around the occluders and out into areas that are not intended to receive the agent. This would result in a reduced concentration of therapeutic agent in the feeder vessels where it is most needed and may also result in therapeutic agent travelling to and detrimentally acting upon unintended tissues. In addition, if the occluders are expanded to too large a size to attempt to prevent leakage, the vessels can be damaged. Further, the release of the therapeutic agent is into the portal vein; however, the size of the opening or openings in the catheter for release of the therapeutic agent is very small in relation to the diameter of the portal vein, further preventing generation of the pressure desired to saturate and penetrate the intended tissues with the therapeutic agent.

As another concern, for long term treatment it may be advantageous to have an implanted port that can be utilized for the repeated administration of a therapeutic treatment to an intravascular site.

U.S. Pub. No. 2017/0319820 to Johnson describes an implantable port adapted to provide localized delivery of a therapeutic treatment directly into the portal vein. The Johnson device includes a three lumen catheter with a first lumen connecting to an anchoring balloon provided at a distal end of the catheter to stabilize location of the distal end of the catheter, a second lumen opening at a distal end of the catheter, and a third lumen opening proximal of the distal end. To applicant's understanding, Johnson does not describe how the second and third lumen are intended to be used, other than for delivery of a therapeutic treatment.

In addition, certain disease states may recommend that patients be treated with targeted radiation in addition to systemic and/or localized therapeutic agents. For example, pancreatic cancer is aggressively treated with both agents and radiotherapy. Targeted radiation requires that fiducial markers be guided, often percutaneously or endoscopically, to adjacent the tissue being treated, to provide a target onto which the radiation beam can be registered and tracked in real-time during the delivery of the radiation dose. Such precisely aimed radiation doses ensure that the tumor receives the optimal dose of radiation with the verified accuracy.

However, the different and separate patient preparations for the therapeutic agent and targeted radiation treatments are taxing to a patient, who is already in a weakened disease state. Further, current fiducial marker delivery technology is less than ideal.

SUMMARY OF THE INVENTION

A dual pathway treatment delivery device is provided. The device includes an implantable delivery port for communication with selected first and second blood vessels for treatment with different therapeutic agents. The first blood vessel is adapted for systemic perfusion, whereas the second blood vessel is adapted to localized perfusion into a selected organ.

In an embodiment, the delivery port has at its proximal end a hub that operably connects to a first lumen and a second lumen. The first lumen is directly open to the first blood vessel but not the second blood vessel, and the second lumen is directly open to the second blood vessel but not the first blood vessel. The first lumen is preferably defined in a first catheter connected with the hub and includes a first distal opening. The second lumen may be defined in the first catheter or a second catheter, and has a second distal opening. The second lumen has a length sufficient such that its second distal opening is at a greater distance from the hub than the first distal opening. Optionally, a dynamic occlusion device may be provided longitudinally displaced from the hub, distally displaced from the first distal opening, along the second lumen, and preferably adjacent the second distal opening.

When a first therapeutic agent is infused at the hub and into the first lumen, the first agent is delivered into the first blood vessel and circulated systemically through the vasculature. When a second therapeutic agent is infused at the hub and into the second lumen, the second agent is delivered regionally to the second blood vessel at a location distal of the first distal opening.

When the second lumen is provided with a dynamic occlusion device adjacent its second distal opening and second therapeutic agent is infused through the hub and into the second lumen, infusion of the second therapeutic agent generates a relative higher fluid pressure on the distal (downstream) side of the dynamic occlusion device than on the proximal (upstream) side of the dynamic occlusion device, and the dynamic occlusion device automatically moves from a closed configuration in which it is displaced from a vessel wall to an open configuration in which it is in contact with the vessel wall. This prevents reflux of the second therapeutic agent, segregating the second therapeutic agent from systemic delivery and permitting the second agent to be delivered with higher pressure than at which the first agent is delivered. Such higher-pressure delivery facilitates deep perfusion of the second therapeutic agent into the small vessels of the selected organ.

In another embodiment, the delivery portion includes a first catheter having a proximal end and a distal end, and an implantable hub provided at the proximal end of the catheter. The first catheter includes first and second lumens. The first lumen has a proximal first end open to a first port of the hub and a distal first opening. The second lumen has a proximal second end open to a second port of the hub and a distal second opening. A second catheter is adapted to be received through the second port and advanced beyond the distal second opening of the second lumen. The second catheter optionally includes a dynamic occlusion device at its distal end. A first therapeutic agent can be infused through the first port and into the first lumen, and circulated systemically through the vasculature. A second therapeutic agent can be infused through the second catheter and beyond its distal end; i.e., to be delivered regionally at a regional location If the second lumen includes a dynamic occlusion device, when the second therapeutic agent is infused through the second port and into the second lumen, the infusion of the agent generates a relative higher fluid pressure on the distal (downstream) side of the dynamic occlusion device than on the proximal (upstream) side of the dynamic occlusion device, and the dynamic occlusion device automatically moves from a closed configuration in which it is displaced from a vessel wall to an open configuration in which it is in contact with the vessel wall, preventing reflux of the second agent, segregating the second therapeutic agent from systemic delivery and circulation, and permitting the second agent to be delivered with higher pressure than at which the first agent is delivered. Such higher-pressure delivery facilitates penetration of the small vessel of the target tissue with the second agent.

The dynamic occlusion device preferably is a microvalve that automatically expands to the diameter of the vessel in which it is deployed when subject to predetermined fluid pressure conditions and contracts to a smaller diameter when subject to relatively lower fluid pressure conditions. A microvalve suitable for use preferably includes a microporous polymer advantageously formed by electrospinning or dip-coating a polymer over a filamentary braid having a frustoconical portion. The microporous polymer allows generation of fluid pressure at one side of the microvalve, while blocking particles on the pressurized side of the microvalve that exceed 5 µm from passing through the microvalve.

In an embodiment, the system also includes at least one pressure-detecting element. The pressure-detecting element may be at least one pressure sensor to sense the fluid pressure at the first and/or second lumens. A pressure-detecting element for the first lumen may be mounted within the port or hub, on or in the first lumen of the catheter, or may be provided on a wire or other device inserted within the first lumen. A pressure-detecting element for the second lumen is preferably adapted for sensing pressure distal of (i.e., downstream of) the dynamic occlusion device. The second pressure-detecting element may be located in the port or hub, on or in the second lumen of the catheter, provided on a wire or other device inserted within the second lumen, on the distal or downstream side of the dynamic occlusion device, or an a wire or other device inserted within the second lumen.

In an embodiment, the first pressure-detecting element allows monitoring of systemic conditions or functions, and the second pressure-detecting element allows monitoring of regional conditions or functions distal of the occlusion device. For example, with respect to a pressure-detecting element located in the portal vein, the pressure monitored can be used to identify conditions that indicate or can be used to prevent liver damage. To that end, a detected high pressure or rising pressure or a measured or calculated significant portosystemic gradient (difference between the portal venous pressure and systemic pressure) may be indicative of cirrhosis of the liver, fatty liver disease, or other liver disease.

In another aspect of the system, the second catheter or lumen is provided with fiducial markers that are adapted to be located adjacent the organ or tumor. The fiducial markers may be in the form of radiopaque marker bands that can be tracked by an image-guided radiotherapy device. As an alternative, the fiducial markers may be located on a guidewire inserted through the second lumen and advanced to the organ necessitating radiotherapy.

In yet another aspect of the system, the second catheter having the fiducial markers, or a guidewire passing within the second catheter, can be shapeable. The shapeable second catheter or guidewire can be activated to cause the second catheter or guidewire to change its shape in three-dimensions. This change in shape repositions the fiducial markers in three dimensions. The dimensional information is used to focus the image-guided radiotherapy device on the treatment location.

BRIEF DESCRIPTION OF THE DRAWINGS

FIG. 1 is a schematic illustration of one embodiment of an implantable, dual pathway therapeutic agent delivery port system.

FIG. 2 is an enlarged schematic illustration across line 2-2 in FIG. 1.

FIG. 3 is an enlarged schematic distal end view of the system of FIG. 1.

FIG. 7 is a schematic illustration of another embodiment of an implantable, dual pathway therapeutic agent delivery port.

FIG. 8 is a schematic illustration of another embodiment of an implantable, dual pathway therapeutic agent delivery port.

FIG. 9 is a schematic illustration showing use at the distal end of another embodiment of an implantable, dual pathway therapeutic agent delivery port provided with a catheter with fiducial markers.

DETAILED DESCRIPTION OF THE PREFERRED EMBODIMENTS

Figure 4:
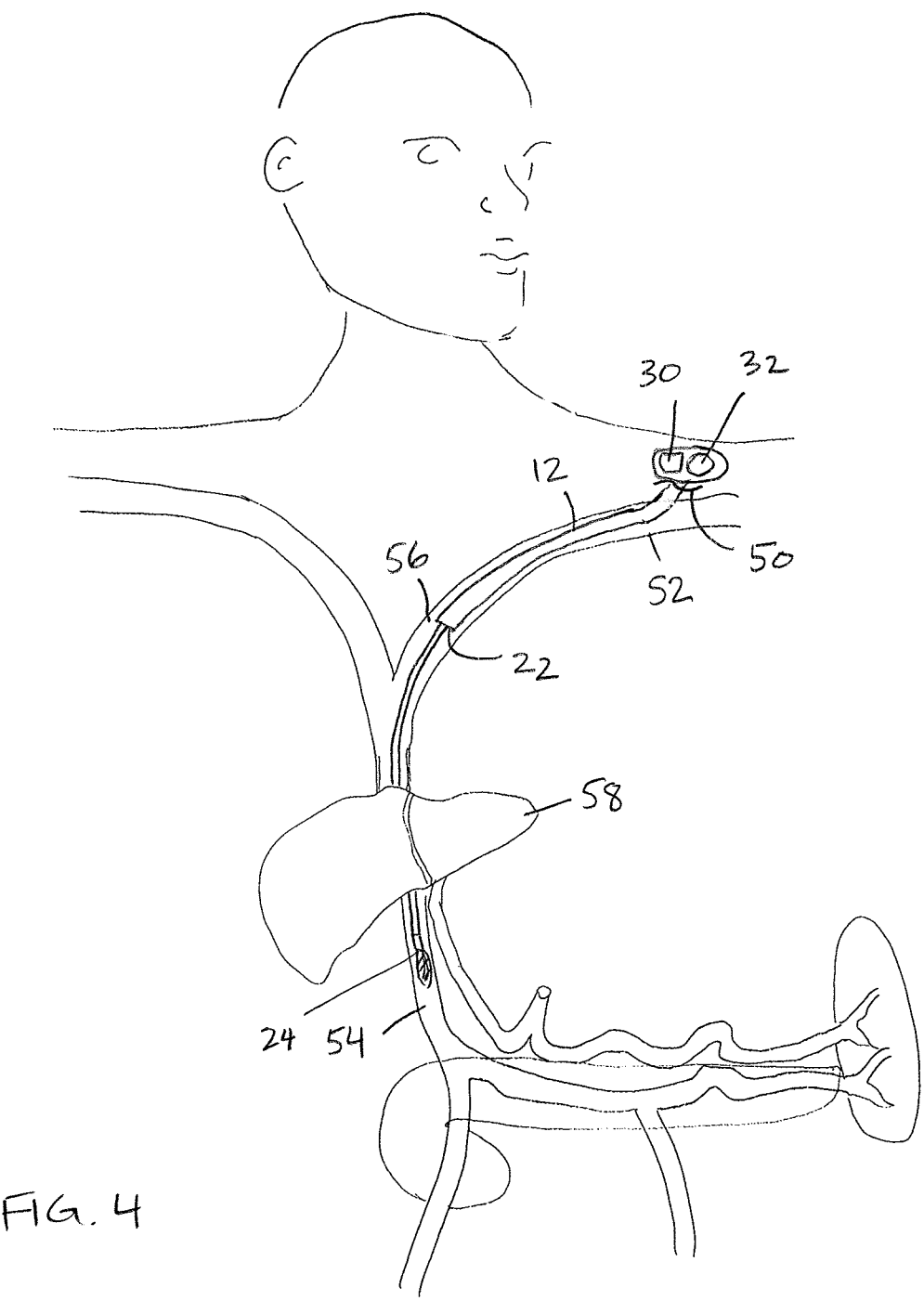
FIGS. 4 and 5 illustrate a method of using an implantable, dual pathway therapeutic agent delivery port.

With reference to the following description, the terms "proximal" and "distal" are defined in reference to an implant site for the hub of the device, described herein, with the term "proximal" being closer to the user's hand, and the term "distal" being further from the implant site such as to be located further within a body of the patient during use.

Apparatus and methods are described herein related to the use of a system to infuse and/or inject one or more therapeutic agents into a mammalian body, including a test subject or a human patient. The apparatus and methods can be used to monitor and treat systemic and/or local conditions by delivering treatments systemically as well as locally. Systemic delivery may be for dispersed conditions or for localized conditions that can be treated via large vessel circulation. In addition, the system can be used to monitor and treat localized conditions of one or more organs. For example, the localized condition may be a solid tumor in an organ. In some cases, the tumor can be a cancerous tumor, such as a tumor specific to, for example, cancer of the pancreas, colon, liver, lung, or uterus. Examples of treatment are provided below.

As described herein, an implantable treatment system is used to provide a first treatment agent for systemic circulation within the body. As also described herein, the implantable treatment system is used to provide a second treatment agent to a localized region of the body in a manner that prevents the second treatment agent from circulating systemically. For example, the localized second treatment agent may be delivered to a solid tumor, to permit targeted treatment of a region by the second treatment agent, isolation of the second treatment agent within the target region, all without isolating a larger region than necessary from blood flow during the treatment procedure. In some cases, the solid tumor is associated with cancer of the pancreas, colon, liver, lung or uterus. With the treatment system in place, the second treatment agent (e.g., an immunotherapy agent, chemoembolization agent, radio-embolization agent) can be injected under pressure into a region of an organ or other defined area of tissue served by one or more feeder vessels. As such, the treatment system is used to deliver the second treatment agent to small tumor feeder vessels connected to a tumor and selectively inject the second treatment agent under pressure into the small tumor feeders.

In an embodiment, the treatment system 10 includes a catheter 12 having a proximal end 14 and a distal end 16. The catheter has a first lumen 18 and a second lumen 20. The first lumen 18 has a first distal opening 22, and the second lumen 20 has a second distal opening 24 that is distally displaced relative to the first distal opening 22. An implantable hub 28 is provided at the proximal end 14 of the catheter. The implantable hub 28 includes a first port 30 in communication with the first lumen 18, and a second port 32 in communication with the second lumen 20. The hub 28 is adapted to be implanted subdermally and is composed of a material that is biocompatible when implanted subdermally to minimize thrombus formation and tissue encapsulation. For example, the hub may be constructed of a styrene-isobutylene-styrene block copolymer. Further, the hub 28 is preferably formed as a generally low-profile housing to prevent pain, discomfort and unsightliness to the recipient patient when implanted. Nevertheless, the hub 28 is adapted to couple to first and second sources of treatment agents to be infused or injected into the first and second ports 30, 32, respectively. The first and second ports 30, 32 may have different sizes, shapes, and/or textures to facilitate subdermal identification of the respective ports. The first and second ports 30, 32 may have different connections, including, by way of example, threaded couplings, leur locks, piercable septums 34, 36, and/or friction connectors at which to receive an infusion or injection of the first and second treatment agents, respectively. By way of example, the first port 30 can be coupled to an infusion pump to administer therapy for extended periods of time. By way of example, the second port 32 can be coupled to a syringe for injection of a bolus of therapy. The first port 30, coupled to the first lumen 18, is preferably adapted to receive low flow infusion such as at 20 mL/hour. The second port 32, coupled to the second lumen 20, is preferably adapted for significantly (order of magnitude) higher rates of infusion, such as 0.1 to 1.0 mL/second (or 360 to 3600 mL/hour). Such rates are exemplar only. However, during retrograde venous infusion into the pancreas and adrenal gland in animal studies, it was determined that infusion should be performed at slower rates to prevent tissue damage. Preferred infusion rates for retrograde venous infusion in the pancreas and adrenal gland is preferably on the order of 0.1-1 ml/minute.

The first distal opening 22 of the first lumen 18 is located proximal of the distal end 16 of the catheter. The second lumen 20 includes a second distal opening 24 at the distal end 16 of the catheter. Further, the first and second lumen 18, 20 may be coaxial lumen of common shape or of different shape, and/or have the same or different cross-sectional areas within the catheter. The first distal opening 22 may be formed by removing at least a portion of the cross-section of the catheter material surrounding the first lumen 18. In such configuration, the catheter 12 has a reduced overall diameter distal of the first distal opening 22. Alternatively, the first lumen 18 may be plugged at a location distal of the first distal opening 22 such that fluid is forced out of the first lumen 18 at the first distal opening 22.

A dynamic occlusion device 40 is coupled to the catheter 12 at a location between the first and second distal openings 22, 24. In a preferred embodiment, the dynamic occlusion device 40 is a filter valve that fully expands to the vessel wall (i.e., reaches an open condition) when the pressure at the second distal opening 24 is greater than the blood pressure. The filter valve 40 is also in a deployed but closed condition (with filter valve retracted away from full contact with the vessel wall) when blood is flowing with pressure greater on the proximal side of the filter valve than on the distal side of the filter valve (i.e., in a proximal to distal direction). In addition, when the radial force of expansion on the filter valve (i.e., the expansion force of the filter valve itself in addition to the force of pressure in the distal vessel over the distal surface area of the valve) is greater than the radial force of compression on the filter valve (i.e., force of pressure in the proximal vessel over the proximal surface area of the filter valve), the filter valve fully expands so that the valve assumes the open configuration. Thus, the radial force of expansion of the filter valve is chosen to be low so that normal blood flow in the downstream distal direction will prevent the deployed filter valve from reaching the open condition. This low expansion force is different than the expansion forces of prior art stents, stent grafts, distal protection filters and other vascular devices, which have significantly higher radial forces of expansion. Thus, once the filter valve is in the deployed configuration in the vessel, the filter valve is dynamically movable (opens and closes) depending on the local fluid pressure about the filter valve: when the fluid pressure is higher on the proximal side of the filter valve, the filter valve assumes a relatively contracted configuration with a first diameter smaller than the diameter of the vessel such that fluid flow about the filter valve is permitted, and when the fluid pressure is higher on the distal side of the filter valve, the filter valve assumes an expanded configuration with a second diameter relatively larger than the first diameter in which the filter valve is adapted to contact the vessel wall.

A filter valve 40 suitable for use in the system includes a filamentary braid 40a coated with a microporous polymer 40b. The microporous polymer 40b allows generation of fluid pressure at one side of the microvalve 40, while blocking particles on the pressurized side of the microvalve that exceed 5 μm from passing through the microvalve. The braid 40a preferably expands into a frustoconical form. The braid 40a is made from metal filaments, polymer filaments, ceramic filaments, glass filaments, radiopaque oxides, or a combination of metal and polymer filaments, which are formed into a substantially frustoconical shape when not subject to outside forces. Where metal filaments are used, the filaments are preferably elastic or superelastic metal such as stainless steel or shape memory nickel-titanium alloy (Nitinol). Where polymeric filaments are utilized, the filaments may be composed of polyethylene terephthalate (PET), polyethylene-napthalate (PEN), liquid crystal polymer, fluorinated polymers, nylon, polyamide or any other suitable polymer. The polymer filaments may be impregnated with a radiopaque agent such as barium sulfate, iodine compounds, radiopaque metallic particles, or other contrast agents to facilitate imaging of the filter valve during use. Iodinated polymeric materials may also be employed as the polymeric filaments. It is desirable that the braid 40' be biased into an expanded configuration at a predetermined force. Therefore, when polymeric filaments are utilized, one or more metal filaments may be utilized in conjunction with the polymeric filaments to provide a desired expansion force to the braid. The diameter of one, more or all of the filaments also can be selected to control the expansion force. In addition, the braid angle can be altered to change the expansion force. Further, as indicated below, the thickness of the polymer coating can be adjusted to alter the expansion force.

The radial force of expansion of a braid is described by Jedwab and Clerc (*Journal of Applied Biomaterials*, Vol. 4, 77-85, 1993) and later updated by DeBeule (DeBeule et al., *Computer Methods in Biomechanics and Biomedical Engineering*, 2005) as:

$$F = 2n\left[\frac{GI_p}{K_3}\left(\frac{2\sin\beta}{K_3} - K_1\right) - \frac{EI\tan\beta}{K_3}\left(\frac{2\cos\beta}{K_3} - K_2\right)\right]$$

where $K_1$, $K_2$, $K_3$ are constants given by:

$$K_1 = \frac{\sin 2\beta_0}{D_0} \quad K_2 = \frac{2\cos^2\beta_0}{D_0} \quad K_3 = \frac{D_0}{\cos\beta_0},$$

and I and $I_p$ are the surface and polar moments of inertia of the braid filaments, E is the Young's modulus of elasticity of the filament, and G is the shear modulus of the filament. These material properties along with the initial braid angle ($\beta_0$), final braid angle ($\beta$), stent diameter ($D_0$), and number of filaments (n) impact the radial force of the braided valve.

The filaments of the braid 40a are not bonded to each other along their lengths to allow the element 40 to rapidly open and close in response to dynamic flow conditions. (The filaments may be coupled together at their proximal ends in a frustoconical construct, or at their proximal and distal ends in a tubular shape.)

As will be appreciated by those skilled in the art, the braid geometry and material properties are intimately related to the radial force and time constant of the valve. Since the valve is useful in vessels of arteries of different diameters and flow conditions, each implementation can have a unique optimization. By way of example only, in one embodiment, the braid has ten filaments, whereas in another embodiment, the braid has forty filaments. Preferably, the filament diameter is chosen in the range of 0.025 mm to 0.127 mm, although other diameters may be utilized. Preferably, the braid angle (i.e., the crossing angle assumed by the filaments in the fully open position—the shape memory position) is chosen in the range of 100° to 150°, although other braid angles may be used. Preferably, the Young's modulus of the filament is at least 100 MPa, and more preferably at least 200 MPa.

The polymer 40b can be coated onto the braid 40a by several methods, including by spraying, spinning, electrospinning, bonding with an adhesive, thermally fusing, mechanically capturing the braid, melt bonding, dip-coating, or any other desired method, to form a filter. The filter can either be a material with pores such as ePTFE, a solid material that has pores added such as polyurethane with laser drilled holes, or the filter can be a web of very thin filaments that are laid onto the braid. Where the polymer filter is a web of thin filaments, the characteristic pore size of the filter can be determined by attempting to pass beads of different diameters through the filter and finding which diameter beads are capable of passing through the filter in large quantities. The very thin filaments can be spun onto a rotating mandrel according to U.S. Pat. No. 4,738,740 with the aid of an electrostatic field or in the absence of an electrostatic field or both. The filter thus formed can be adhered to the braid structure with an adhesive or the braid can be placed on the mandrel and the filter spun over it, or under it, or both over and under the braid to essentially capture it. The filter can have some pores formed from spraying or electrospinning and then a secondary step where pores are laser drilled or formed by a secondary operation. In one embodiment a material capable of being electrostatically deposited or spun is used to form a filter on the braid, with the preferred material being capable of bonding to itself. The filter may be made of polyurethane, pellethane, polyolefin, polyester, fluoropolymers, acrylic polymers, acrylates, polycarbonates, or other suitable material. The polymer is spun onto the braid in a wet state, and therefore it is desirable that the polymer be soluble in a solvent. In the preferred embodiment, the filter is formed from polyurethane which is soluble in dimethylacetamide. The polymer material is spun onto the braid in a liquid state, with a preferred concentration of 5-20% solids for an electrostatic spin process and 15-25% solids for a wet spin process.

As another alternative construct for polymer-coating the braid, the braid can be dip-coated to form a filter onto the braid. The braid is mounted on a mandrel having the same outer diameter as the inner diameter of the fully expanded braid. The mandrel is preferably polytetrafluoroethylene (PTFE)-coated steel, in which the PTFE acts as a release surface. Alternatively, a non-coated mandrel may be used. It is important that inner diameter of the braid and the outer diameter of the mandrel not be spaced from each other when the braid is mounted on the mandrel. Thus, they preferably have a common diameter within a tolerance of ±0.065 mm. Keeping the entire inner braid in contact with the mandrel allows for the filaments to be evenly coated with the polymer, as subsequently described, so that the filter valve expands uniformly after the polymer dries. Alternately, the braid can be mounted on an oversized mandrel (greater than the inner diameter of the braid), but such will result in an increase in the braid angle of the filaments, and thereby resize the filter valve and effect the expansion force thereof. In an alternate arrangement the braid may be mounted within a tubular mandrel having the same size as the outer diameter of the braid, provided with like tolerances described above. As yet another alternative, the braid can be mounted inside an undersized tubular mandrel (having an inner diameter smaller than the outer diameter of the braid), but such will result in a decrease in the braid angle of the filaments, and thereby also resize the filter valve and effect the expansion force thereof. The type of mandrel (solid or tubular), and the location of the braid thereon (external or internal), will effect localization of the polymer on the braid (providing a smooth internally coated filter valve for external mounting on a solid mandrel and providing a smooth externally coated filter valve for internally mounting within a tubular mandrel), and thereby alter areas of lubricity for the resulting filter valve.

Once the braid is tightly mounted on (or within) the mandrel, the braid is dip coated into a polymer solution at a controlled steady rate. The solution is an elastomeric thermoplastic polymer dissolved in a solvent system with a vapor point ranging from 30-200° C. to produce a solution with a dynamic viscosity range of 50-10,000 cP. The rate of decent and accent is inversely dependent upon the viscosity of the solution and ranges from 1-100 mm/sec. The rate is critical to provide an even coating of the polymer on the braid, to allow wetting of all surfaces of the braid even at locations where the braid filaments are in contact with the mandrel and consequent wicking of the polymer coating into the braid particularly to the surface in contact with the mandrel, and to release air bubbles that may be trapped during the dipping process. By way of example, in one embodiment of the method for dipping into a pellethane solution (pellethane dissolved in the solvents dimethylacetamide (DMA) and tetrahydrofuran (THF)), the rate is such that the dwell time of a 135 mm (6 inch) braid is 16 seconds. The rate is also preferably such that the polymer wicks down the length of the entire braid during withdrawal of the braid from the solution. The braid is dipped one time only into the solution to limit the thickness of the coating and thereby prevent restraint on the braid filaments and/or control smoothness of the polymer coating membrane. The controlled rate may be controlled by coupling the mandrel to a mechanized apparatus that dips and raises the braid on the mandrel at the steady and controlled rate into the polymer solution.

After the braid is withdrawn from the polymer solution, the solvent is evaporated over a time frame relative and temperature range corresponding to the solvent boiling point, with higher temperatures and longer durations utilized for high vapor point solvents. All preferred polymer solutions use some DMA to control the uniformity of the coating thickness, and may use THF to control the rate of solvent evaporation. The ratio of high vapor point solvents such as DMA to low vapor point solvents such as THF allows for control over the rate of transition from a lower viscosity high solvent content polymer solution to a high viscosity low solvent content polymer solution to a solid solvent free material, affecting the quality of the polymer membrane. In one method, the solvents are released in an oven heated to a temperature above the boiling point of DMA (165° C.) in order to rapidly release the DMA. A preferred time of heating at this temperature is 5 minutes which is sufficient to release the DMA. It is appreciated that THF has a substantially lower boiling point (66° C.) and will vaporize quickly without such substantial heating. Alternatively, the polymer-coated braid can be oven heated at a temperature below the boiling point of DMA, e.g., 80° C.-100° C., which will release of the DMA from the coated braid, but at a slower rate than would occur above the boiling point of DMA. This temperature rapidly drives off the DMA while keeping the coating braid safely below the melting or softening point of the braid. A preferred time of heating at this temperature is 10 minutes which is sufficient to release the DMA. As yet another alternative, the polymer-coated braid can be allowed to dry ambient room temperature, which results in DMA release occurring at a slower rate than each of the above.

After the solvents have been released from the polymer-coated braid, the coated braid is cooled below the glass transition temperature of the polymer to plasticize the polymer on the braid. Once cooled, the coated braid is released from the mandrel. If the mandrel is coated with PTFE, the braid may self-release from the mandrel or may be readily released. If the mandrel is uncoated, a release agent such as isopropyl alcohol (IPA) may be used to facilitate removal of the coated braid from the mandrel. The resulting elastomeric membrane filter formed on the braid may be elastically deformed over a range of 100-1000% elongation. In addition to pellethane, the membrane may be formed from, but not limited to, other thermoplastic elastomers including other urethanes such as aliphatic polyether-based thermoplastic polyurethanes (TPUs), and styrene-isoprene-butadiene-styrene (SIBS). These polymers may be dissolved in appropriate solvents or heated to their melting point to form a fluid.

Dynamic filter valves 40 suitable for use with the treatment system 10 are described in detail in U.S. Pat. Nos. 8,500,775, 8,696,698, 8,696,699, 9,539,081, 9,770,319, and 9,808,332, as well as in US Pub. Nos. 2018055620 and 20160256626, and further in U.S. Ser. No. 15/464,036, all of which are hereby incorporated by reference herein in their entireties.

The system 10 preferably includes at least one of a first pressure-detecting element 42 adapted to sense the fluid pressure at the first lumen 18, and a second pressure-detecting element 44 adapted to second pressure in the second lumen 20; i.e., distal of or at the downstream side of the dynamic occlusion device 40. Each of the pressure-detecting elements 42, 44 may be mounted within the port in fluid communication with the first and second lumen 18, 20, or on or in the catheter, or may be provided as a sensor on a wire 46 or other device inserted within the respective lumen.

Turning now to FIG. 4, in one method of use, the treatment system 10 is inserted into the patient through a puncture incision 50 and into the vascular system 52. In an exemplar method, the catheter 12 is inserted along a venous track. The distal end of the catheter is advanced to a target location. By way of example, the target location may be the portal vein 54. When the distal end of the catheter is at the target location, the first distal opening 22 is preferably located in the superior vena cava 56. Thus, the catheter 12 has a length sufficient to extend from the incision 50 to the portal vein 54, and the first and second distal openings 22, 24 are spaced apart to position the first and second distal openings 22, 24 at the respective target locations.

The first pressure-detecting element 42 is used to monitor systemic pressure. The second pressure-detecting element 44 is used to monitor pressure at the target location. Because the portal vein 54 is a pathway that provides a significant portion of the blood flow to the liver 58, the second pressure-detecting element 44 allows monitoring of regional pressure conditions at the liver. For example, the second pressure-detecting element 44 in the portal vein 54 can be used to identify conditions that indicate or can be used to prevent liver damage. To that end, a detected high pressure or rising pressure may be indicative of cirrhosis of the liver, fatty liver disease, or another disease state of the liver.

Before operating the pressure sensors to detect in vivo pressures, or using the detected pressures to determine an in vivo portosystemic gradient, the pressures sensors should be calibrated to a reference pressure. The sensors are preferably calibrated to pressure using one of several techniques.

Each sensor may be calibrated to atmosphere to achieve absolute pressure measurements. This can be accomplished by opening a fluid channel to air, using a syringe needle in the port, while occluding the distal end of the catheter. Such method thus requires a mechanism for occluding the catheter end during calibration, and thus necessitates that the sensor be within the catheter lumen or within the port housing in fluid communication with the catheters. A second method of calibration using relative measurements obtained by calibrating the sensor on the second catheter (in the portal system) relative to the sensor on the first catheter (within systemic circulation). The difference or the portosystemic gradient required to assess, e.g., fatty liver disease. In a third method, two sensors are placed on the second catheter, one to measure and one to act as reference.

A first treatment agent can be infused or injected at a relatively low flow rate into the patient via the first port 30 for systemic circulation. For systemic circulation, high pressure higher flow rates and higher developed pressures for infusion are not required. A slow drip or release rate via the first port 30, the first lumen 18, and out of the first distal opening 22 can be effective. A second treatment agent be injected into the patient through the second port 32 and the second lumen 20, out of the second distal opening 24, and into the portal vein 54 for delivery to the pancreas, spleen or liver. The second treatment can be injected as a bolus at a relatively higher flow rate than the first agent. In conjunction with the dynamic occlusion device 40, such injection through the second lumen 20 and out of the second distal opening 24 can be made under significantly higher pressure than infusion through the first lumen 18.

Figure 5:
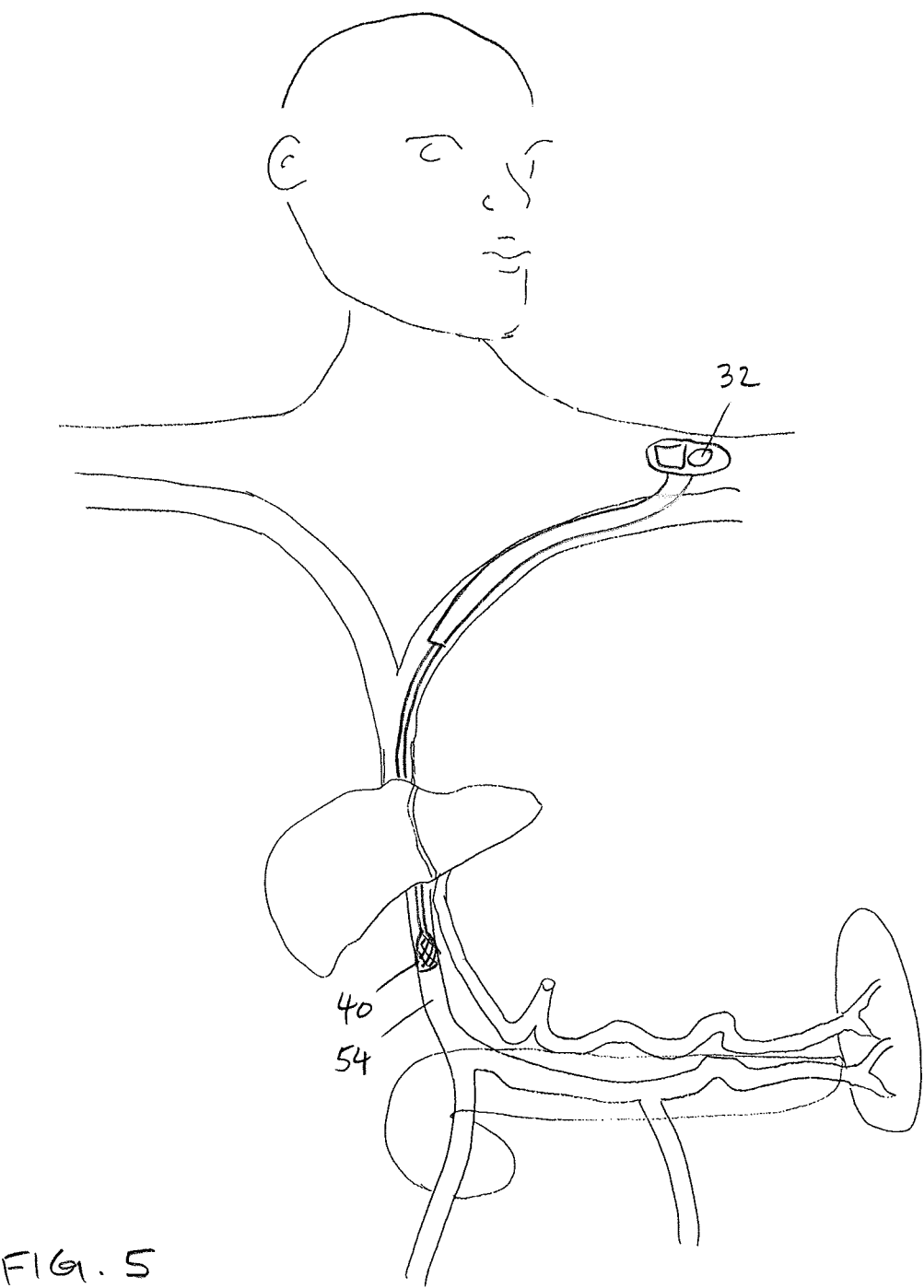

Turning to FIG. 5, when the second treatment agent is injected through the second port 32, the pressure in the downstream delivery vessel is increased above systemic pressure causing the dynamic occlusion device 40 to expand into an open configuration and block the vessel 54. With the vessel 54 blocked upstream, the treatment agent is forced under pressure downstream into a target organ, such as the pancreas, spleen or liver. Such higher-pressure delivery facilitates deep penetration of the second treatment agent into the small vessels of the target organ, as well as generates a longer dwell time of the second treatment agent within the target organ. Further, the bolus of medication through the second port 32 can be followed up with a bolus of saline under a relatively higher pressure to advance the flow of the second therapeutic agent into the target vessels under a relatively higher pressure than that which it was originally infused; i.e., to provide reduced stress to the medication while passing through the catheter, yet provide reproducible cannulization into the target organs and tissues, and deep penetration of the medication into the target vessels.

Figure 6:
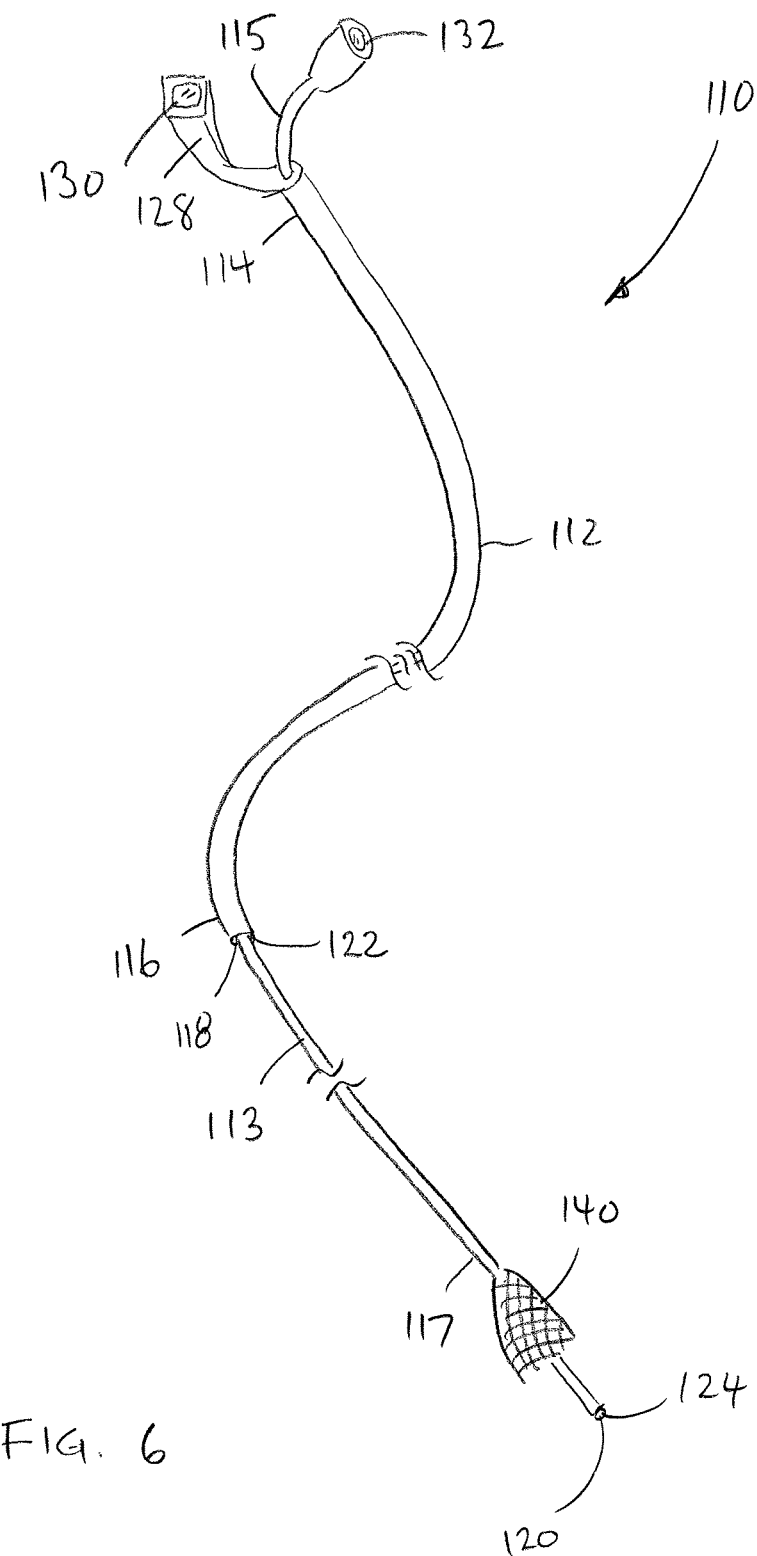
FIG. 6 is a schematic illustration of another embodiment of an implantable, dual pathway therapeutic agent delivery port.

Turning now to FIG. 6, another embodiment of a treatment system 110 is shown. The treatment system includes a first catheter 112 having a proximal end 114 and a distal end 116. The first catheter 112 has a first lumen 118 with a first distal opening 122. An implantable hub 128 is provided at the proximal end 114 of the first catheter. The implantable hub 128 includes a first port 130 in communication with the first lumen 118. The hub 128 is adapted to be implanted subdermally. The first catheter 112 has a length between the hub 128 and first distal opening 122 that permits the hub to be implanted at an access site, and the distal end 116 of the catheter to be delivered into a relatively large venous site such that it is subject to consistent systemic circulation. A first pressure sensor (not shown) is provided to sense a pressure in the first lumen 118 of the first catheter 112.

The system 110 also includes a second catheter 113 defining a second lumen 120, and a second distal opening in 124 communication with the second lumen. A dynamic occlusion device 140 is provided at the distal end 117 of the second catheter 113. The second distal opening 124 opens distal of or within the dynamic occlusion device 140. By way of example, the dynamic occlusion device 140 may be any of the devices described in U.S. Pat. Nos. 8,500,775, 8,696,698, 8,696,699, 9,539,081, 9,770,319, and 9,808,332, as well as in US Pub. Nos. 2018055620 and 20160256626, and further in U.S. Ser. No. 15/464,036, all of which are hereby incorporated by reference herein in their entireties. The proximal end 115 of the second catheter 113 includes a port 132 adapted to be coupled to a source of a treatment agent that can be delivered at a relatively high pressure; i.e., substantially higher pressure than the first port 130, and up to and beyond an order of magnitude higher pressure. A second pressure sensor (not shown) is provided to sense a pressure within the second lumen 120 of the second catheter 113.

In use, the first catheter 112 is delivered through an incision to a venous location such that the first distal opening 122 is open to system circulation and system venous pressures. The first distal opening 122 may be located in the superior vena cava. The second catheter 113 is then advanced through the hub 128 so that the second distal opening 117 of the second catheter is displaced beyond the distal end 116 of the first catheter.

A first therapeutic agent may be delivered through the first lumen 118 of the first catheter 112. Systemic pressure may be measured via the first pressure sensor. A second therapeutic agent may be delivered through the second lumen to a target location distal of the first distal opening 122. More specifically, the second therapeutic agent may be delivered to a restricted tissue location. Further, the second therapeutic agent can be delivered at a relatively higher fluid pressure. The second therapeutic agent is delivered on the distal (downstream) side of the dynamic occlusion device 140, and the pressure of the therapeutic delivery automatically moves the dynamic occlusion device 140 from a closed configuration in which it is displaced from a vessel wall to an open configuration in which it is in contact with the vessel wall, preventing reflux of the second therapeutic agent, segregating the second therapeutic agent from systemic delivery, and permitting the second therapeutic agent to be delivered with higher pressure than at which the first therapeutic agent is delivered. Such higher-pressure delivery facilitates penetration of the small vessel of the target tissue with the second therapeutic agent.

Turning now to FIG. 7, another embodiment of a treatment system 210 is shown. The treatment system 210 includes a first catheter 212 having a proximal end 214 and a distal end 216. The first catheter 212 has a first lumen 218 with a first distal opening 222, and a second lumen 220 with a second distal opening 224. An implantable hub 228 is provided at the proximal end 214 of the first catheter. The implantable hub 228 includes first and second ports 230, 232 in communication with the first and second lumen 218, 220, respectively. The hub 228 is adapted to be implanted subdermally. The first catheter 212 has a length between the hub 228 and first distal opening 222 that permits the hub to be implanted at an access site and the first distal opening 222 to be delivered into a relatively large venous site such that it is subject to consistent systemic circulation. By way of example, the length of the first catheter 212 between the hub 228 and the first distal opening 222 is sufficient to extend subdermally from an implant site (near the clavicle) to the superior vena cava (SVC). The first catheter 212 has a length between the hub 228 and second distal opening 224 that permits the second distal opening 224 to be intravascularly located, and more preferably intravenously located, at a selected organ. By way of example, the length of the first catheter 212 between the hub 228 and the second distal opening 224 is sufficient to extend subdermally from an implant site (near the clavicle) into the portal vein. Pressure sensors (not shown) are provided to sense pressures in the first and second lumen 218, 220.

In use, the first catheter 212 is delivered through an incision to a venous location such that the first distal opening 222 is open to systemic circulation and systemic venous pressures. The first distal opening 222 may be located in the superior vena cava, and the second distal opening 224 is located at or adjacent a major vein leading from a target organ, such as the pancreas (or the liver or the adrenal gland, depending on the location of the second distal opening). The first lumen 218 can be used to periodically deliver a systemic therapeutic treatment. The second lumen 220 can be used to deliver a targeted therapeutic treatment to the target organ. Therapeutic delivery can be regulated based on sensed pressure in one or both of the first and second lumen.

Referring now to FIG. 8, another embodiment of a treatment system 310 is shown. The treatment system 310 includes an implantable hub 328, a first catheter 312 extending from the hub, and a second catheter 314. The first catheter 312 has a proximal end 314 and a distal end 316, a first lumen 318 defined between its ends, and a first distal opening 322 at the distal end of the first lumen 318. The second catheter 313 is preferably introducible through a port 332 in the hub 328, longitudinally displaceable relative to the hub 328, and preferably removable from the hub. The second catheter 313 has a second lumen 320 with a second distal opening 324 at its distal end 317. The first catheter 312 has a length between the hub 328 and its distal opening 322 that permits the hub to be implanted at an access site, and the distal end 322 of the first catheter to be located within a relatively large venous site such that it is subject to consistent systemic circulation. The second catheter 313 has a length between the hub 328 and its distal opening 324 that permits it to be intravenously located at a selected organ. Pressure sensors (not shown) are provided to sense systemic and localized pressures relative to the first and second lumen 318, 320, respectively.

In use, the first catheter 312 is delivered through an incision to a venous location such that the first distal opening 318 is open to systemic circulation and systemic venous pressures. The first distal opening 318 may be located in the superior vena cava. The second catheter 313 is then advanced through the port in the hub 328 and intravenously traversed to a target location at the venous outlet of a target organ. At a first time a first therapeutic agent is systemically delivered through the first lumen of the first catheter 312. At a second time a second therapeutic agent is delivered locally to the target organ through the second lumen 320 of the second catheter 313. The first and second agents may be the same or different. The first and second times may occur periodically, or alternate. The first and second times may occur at different periods, with either of the first or second times occurring with greater frequency. The first and second therapeutic agents may be the same or different. The first therapeutic agent may be a chemotherapy agent; the second therapeutic agent may be a living cell therapy. At the completion of each or all treatments with the second therapeutic agent, the second catheter 313 may be withdrawn from the hub 328, while the hub 328 and first catheter 312 remain implanted in the patient. Similar therapeutic delivery can be carried out with any of the described embodiments.

Turning now to FIGS. 13 through 16, another embodiment of an implantable hub 828 is shown. The hub 828 includes a first port 830 and a second port 832. The first port 830 is preferably defined by a first pierceable, self-healing septum 834 and a first reservoir 833, with the first reservoir 833 in fluid communication with a first lumen connector 842. The second port 832 is preferably defined by a second reservoir 837, a second septum 836 covering the second reservoir 837, and a valved opening 835 separate from the second septum 836. The second septum 836 is a pierceable, self-healing material that covers entry into the second reservoir 837. The valved opening 835 is directed in-line with a second lumen connector 844. The valved opening 835 preferably has a funnel shaped mouth 835a, generally tapering inward toward the valve 835b to guide a device into the mouth and toward the valve. The valve 835b is preferably a slit valve or appropriate alternative that permits opening upon the force of insertion of a device through the valve, and self-closing once the device is removed. The mouth 835a, the valve 835b, the second reservoir 837, and the second catheter connector 844 are located substantially in-line with each other such that an instrument can be guided into the mouth, through the valve, into the second reservoir, and out of the second catheter connector. Whereas the second septum 836 is provided at a top 828a of the hub 828, the opening 835 may be provided within a side wall 828b of the hub such that infusion through the second septum 836 and insertion of a device through the opening 835 can occur along relatively transverse or oblique axes $A_1$, $A_2$. At least the second reservoir 837, and preferably each of the first and second reservoirs 833, 837, is provided with a respective pressure sensor 839.

Figure 18:
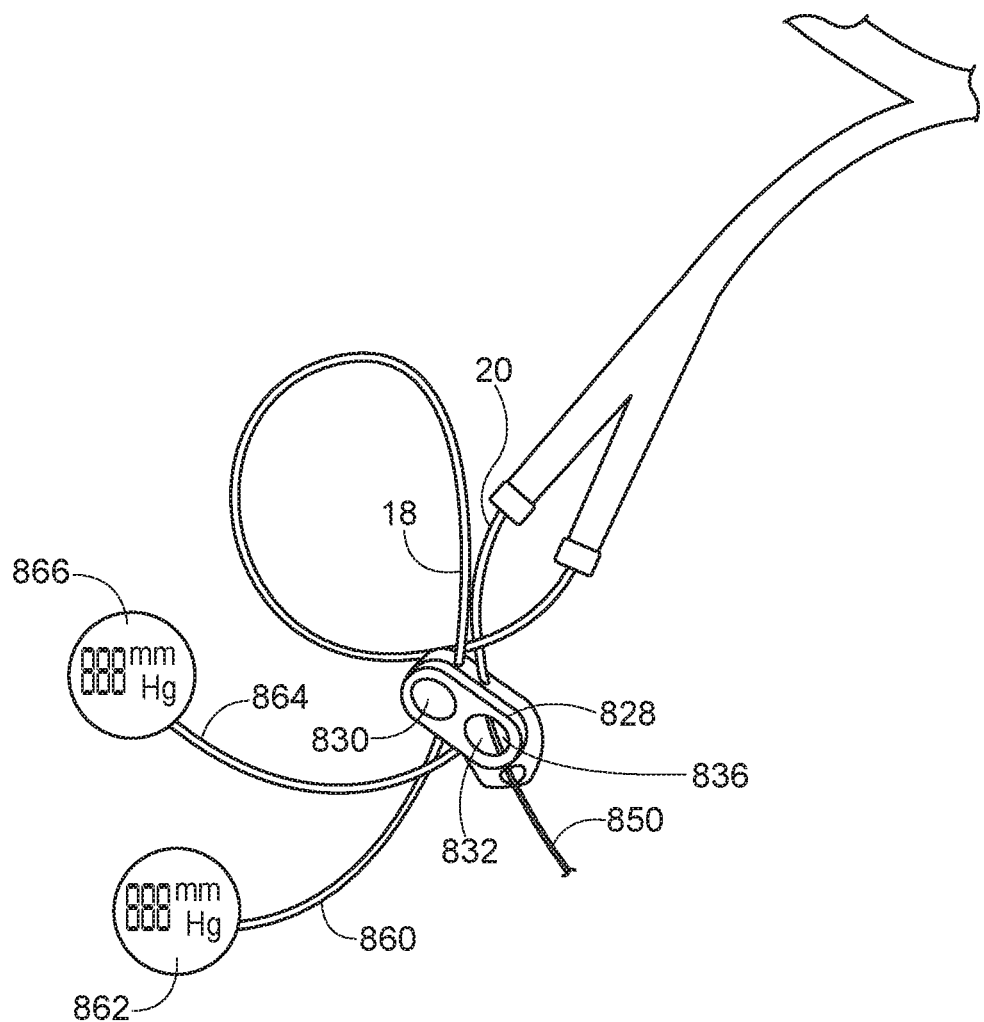
FIG. 18 is a top view of the hub shown in FIGS. 13 through 16 as part of a more complete implantable treatment system for delivering a therapeutic treatment to a patient.

Turning now to FIGS. 18 and 19, the first and second lumen connectors 842, 844 are connected to respective first and second catheters 18, 20. The first catheter is preferably implanted into a vessel communicating to deliver fluid into systemic circulation, whereas the second catheter is implanted to into a vessel communicating directly or closely with a target organ. More preferably, the opening at the distal end of the first catheter is implanted into a venous conduit at or near the heart, such the hepatic vein, superior vena cava, inferior vena cava, or right atrium, and the opening at the distal end of the second catheter is implanted into a vein of the target organ.

With the port 828 and first and second catheters 18, 20 implanted in the patient, the first therapeutic agent is delivered via the first port 830 into systemic circulation. The second therapeutic agent is delivered by syringe (not shown) through a small puncture in the skin, through the first septum 834, and into a first reservoir (not shown). The therapeutic agent flows from the first reservoir through the first catheter 18 and out into preferably venous side, systemic circulation. The first sensor in the first reservoir senses and indicates general venous pressure conditions during agent delivery. The first pressure sensor is preferably coupled via a first link, such as wires 860 or a wireless connection, to a first display 862.

In addition, a therapeutic infusion device 850 in the form of a catheter with an occluder (not shown) provided at its distal end can be inserted through a small incision and advanced into the mouth of the second port 832, through the valve 835b, into the second reservoir 837, and out into the second catheter 20, where it is advanced to a locus of targeted therapeutic treatment. A second therapeutic agent is then delivered through the infusion device 850 and to the locus of treatment within the patient on the distal side of the occluder such that the occluder prevents reflux of the second therapeutic agent. A pressure sensor on the infusion device 850 can sense and indicate local pressure conditions in the vessel at the delivery site. The therapeutic infusion device 850 can be removed from the second port 832 after delivery of the second therapeutic agent. Alternatively, the therapeutic infusion device can be coupled to an injection pump for metered or otherwise controlled infusion of the second therapeutic agent over time.

In another method of treatment, the infusion device 850 is not necessarily required for local delivery of the second therapeutic agent to the target organ. Rather, the second therapeutic agent is delivered by syringe (not shown) through a small puncture in the skin, through the second septum 836, and into the second reservoir 837. The second therapeutic agent flows from the second reservoir 837 through the lumen of the second catheter 20 and to the delivery site. The second sensor 839 in the second reservoir 837 senses and indicates local pressure conditions in the vessel during delivery of the second therapeutic agent. The second pressure sensor 839 is preferably coupled via a second link, such as wires 864 or a wireless connection, to a second display 866.

Further, in any of the embodiments, the pressure sensors can be physically coupled to electronics at the hub and indicators that directly access the pressure readings. Alternatively, the pressure sensors or associated circuitry in the hub can be wirelessly coupled to indicators, such as displays that read the sensed pressures without direct access to the treatment system. Such wireless systems can be inductively charged using suitably antennas, batteries, and charging elements.

The pressure sensors can electrical sensors. Alternatively, the pressure sensors can be fiber optic sensors that sense pressure correlated to an optical displacement. The physics of such systems are well-known. One advantage of a fiber optic system is that the catheters may be sized by cutting material on the proximal side of the device. The fiber optic cable uses a single light channel to process pressure changes and may be easier to reconnect with a processing unit in the port than the multiple small wires used in electrical systems.

It has been noted that patients with certain diseases are aggressively treated with both therapeutic agents and targeted radiation. The foregoing addressed how to facilitate both systemic and/or localized infusible therapeutic agents. However, pancreatic cancer is aggressively treated with both therapeutic agents and radiotherapy. In accord with another aspect of the system, combination treatments with systemic and/or localized therapeutic treatments, as well as targeted radiation is facilitated.

Turning now to FIG. 9, another embodiment of a treatment system 410 is shown. The treatment system 410 includes an implantable hub (not shown, but it can be similar to any of hubs 28, 128, 228, 328, 828), a first catheter 412 extending from the hub, and a second catheter 413. The second catheter 413 has a second distal opening 424 at its distal end 417. The first catheter 412 has a length between the hub and its distal opening 422 that permits the hub to be implanted at an access site, and the distal end 422 of the first catheter 412 to be located within a relatively large venous site such that it is subject to consistent systemic circulation. The second catheter 413 has a length between the hub and its distal opening 424 that permits it to be intravenously located at a selected organ, such as within the portal vein to treat the pancreas 448. As described above, pressure sensors are provided to sense systemic and localized pressures relative to the first and second distal openings 422, 424, respectively. In order to facilitate targeted radiation, the second catheter is provided with a series of a fiducial markers 450. The markers 450 are preferably radiopaque and/or otherwise adapted to be visible by an imaging system on an image-guided radiotherapy treatment device. The markers may be bands, beads, or tags. The markers 450 may be rotationally uniform (such as a cylindrical tube), and/or may have a constant cross-sectional linear shape (such as a rectangular tube about the catheter wall, or may be wire-like elements extending within the side wall of the second catheter 413, or may be non-uniform in cross-sectional area along their length such that each marker provides information on its individual orientation when imaged, or may each have a different size and/or shape. When the markers 450 on the second catheter 413 are located inside a venous tract, such as the portal vein, of the patient, the markers can be brought into close proximity with the cancerous tissue 452 required to be treated. "Close proximity" for purposes herein means within 10 mm, and more preferably within 1-5 mm. The imaging system can then accurately track the markers 450 as reference points in real-time to target delivery of a radiation dose even as the pancreas 448 and associated cancer tissue 452 move slightly during respiration or other movement.

Figure 10:
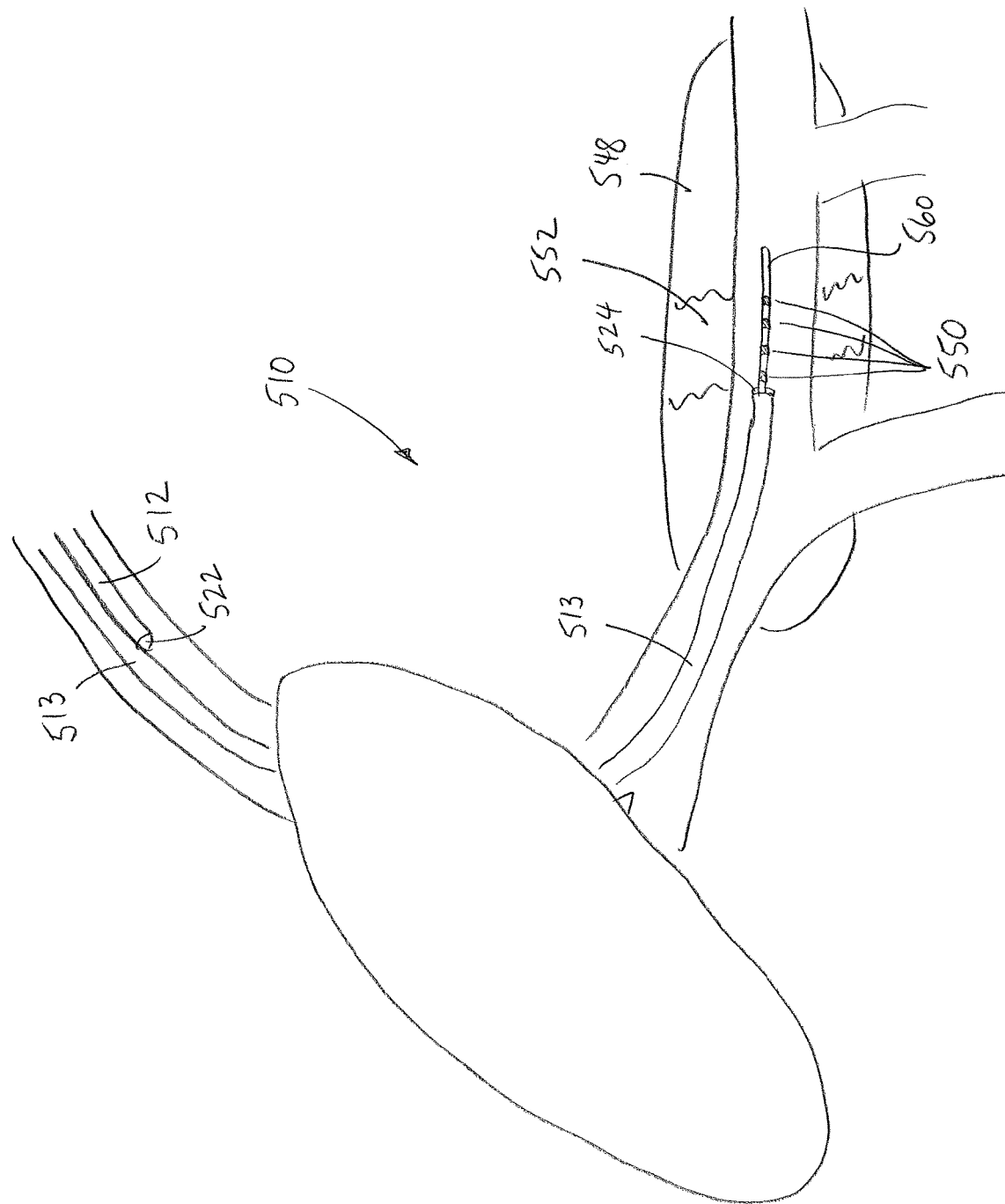
FIG. 10 is a schematic illustration showing use at the distal end of another embodiment of an implantable, dual pathway therapeutic agent delivery port in combination with a guidewire with fiducial markers.

Turning now to FIG. 10, another embodiment of a treatment system 510 is shown. The treatment system 510 includes an implantable hub (not shown, but it can be similar to any of hubs 28, 128, 228, 328, 828), a first catheter 512 extending from the hub, and a second catheter 513. The second catheter 513 has a second distal opening 524 at its distal end 517. The first catheter 512 has a length between the hub and its distal opening 522 that permits the hub to be implanted at an access site, and the distal end 522 of the first catheter 512 to be located within a relatively large venous site such that it is subject to consistent systemic circulation. The second catheter 513 has a length between the hub and its distal opening 524 that permits it to be intravenously located at a selected organ, such as within the portal vein to treat the pancreas 548. As described above, pressure sensors are provided to sense systemic and localized pressures relative to the first and second distal openings 522, 524, respectively. In order to facilitate targeted radiation, a guidewire 560, provided with a series of a fiducial markers 550 along its distal end, is provided into the second catheter and in alignment with the cancerous tissue 552 that is desired to be treated with targeted radiation. The imaging system can then track the markers 550 even as the pancreas 548 and associated cancer tissue 552 slightly move during respiration or other slight movements.

Figure 11:
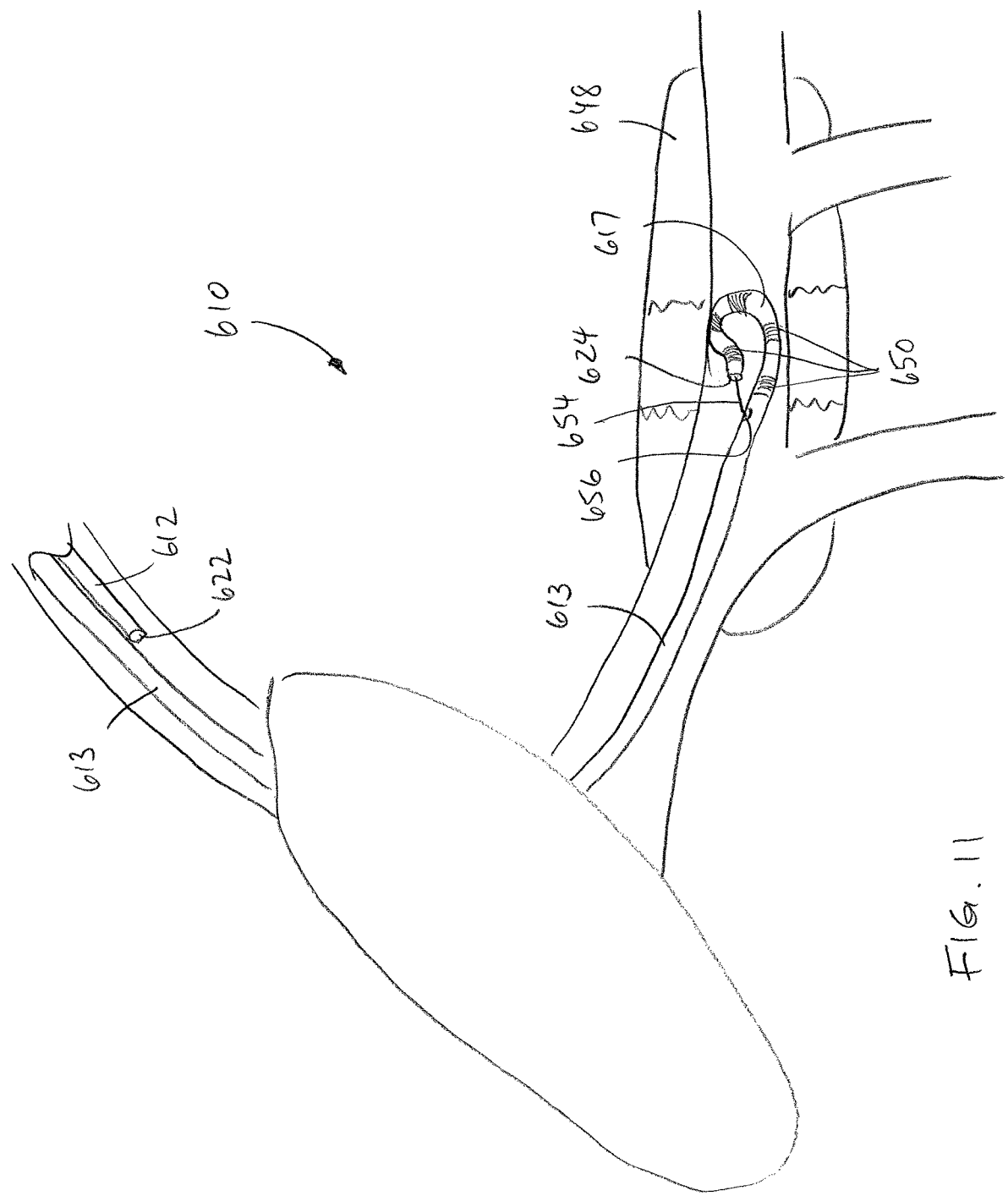
FIG. 11 is a schematic illustration showing use at the distal end of another embodiment of an implantable, dual pathway therapeutic agent delivery port provided with a shapeable catheter with fiducial markers.

Turning now to FIG. 11, another embodiment of a treatment system 610 is shown. The treatment system 610 includes an implantable hub (not shown, but it can be similar to any of hubs 28, 128, 228, 328, 828), a first catheter 612 extending from the hub, and a second catheter 613. The second catheter 613 has a second distal opening 624 at its distal end 617. The first catheter 612 has a length between the hub and its distal opening 622 that permits the hub to be implanted at an access site, and the distal end 622 of the first catheter 612 to be located within a relatively large venous site such that it is subject to consistent systemic circulation. The second catheter 613 has a length between the hub and its distal opening 624 that permits it to be intravenously located at a selected organ, such as within the portal vein to treat the pancreas 648. As described above, pressure sensors are provided to sense systemic and localized pressures relative to the first and second distal openings 622, 624, respectively. In order to facilitate targeted radiation, the second catheter is provided with a series of a fiducial markers 650, as described with respect to FIG. 9. In addition, the tip of the second catheter 613 is coupled to a control wire 654 that extends back to the proximal end of the second catheter. The control wire 654 may be incorporated into a handle or coupled to the hub. When the proximal end of the control wire 654 is actuated to pull the distal end of the control wire relative to the distal end of the second catheter 613, the distal end 617 of the second catheter changes shape in three dimensions to reposition the fiducial markers 650 in three dimensions. The second catheter 650 may include weaknesses in the catheter wall that biases how the distal end of the second catheter will change shape when subject to the force of the actuation wire 654. For example, the distal end 617 of the second catheter 613 may take the form of a three-dimensional loop or a coil. The dimensional information is used by the image-guided radiotherapy device to focus the treatment to the treatment site. Particularly where the second catheter is also used to deliver a localized therapeutic treatment, the second catheter may include a seal 656 through which the actuation wire 654 returns into the lumen of the second catheter 613 to prevent inadvertent leakage of the therapeutic treatment other than from the distal opening 624.

Figure 12:
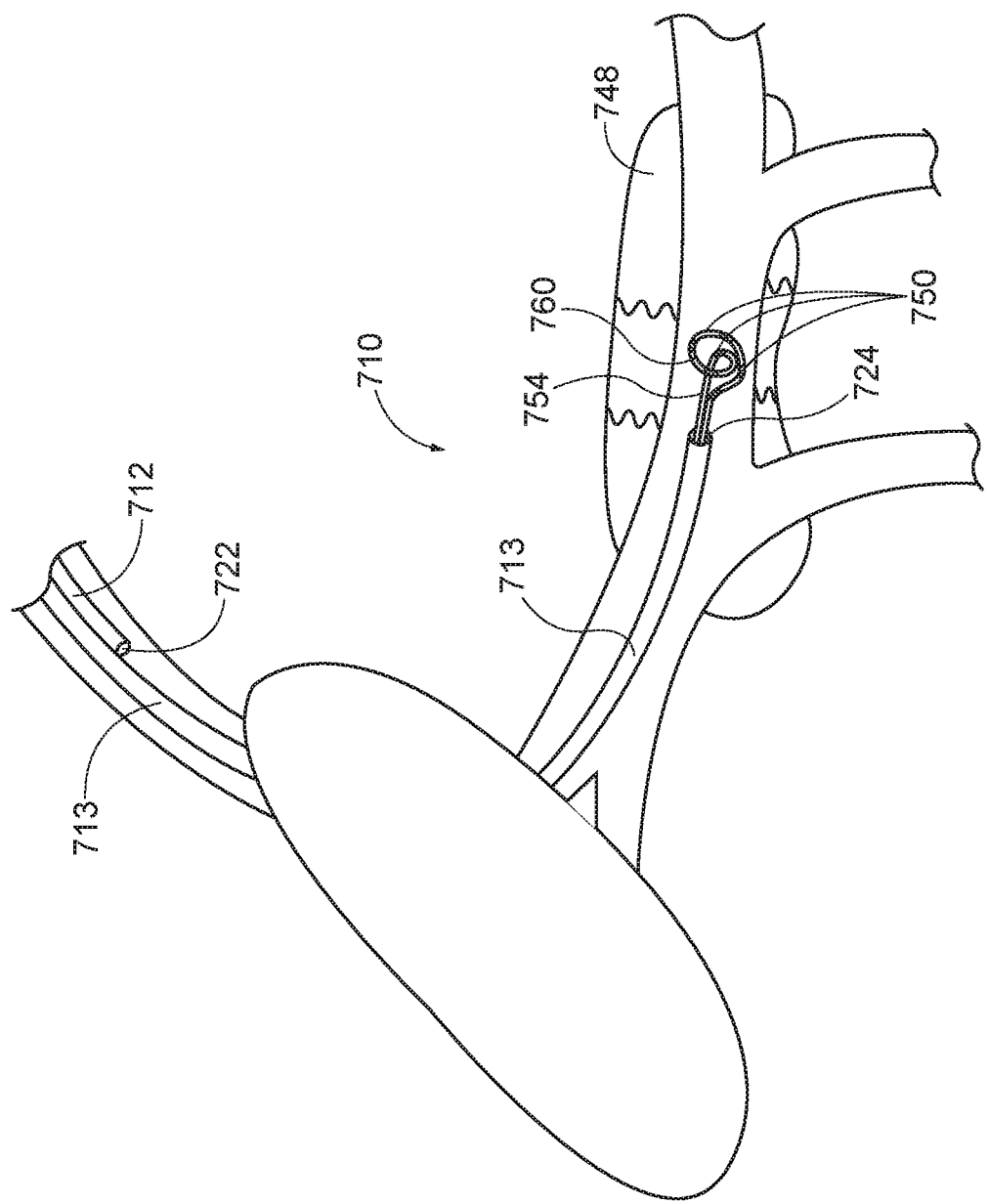
FIG. 12 is a schematic illustration showing use at the distal end of another embodiment of an implantable, dual pathway therapeutic agent delivery port in combination with a shapeable guidewire with fiducial markers.
Figure 14:
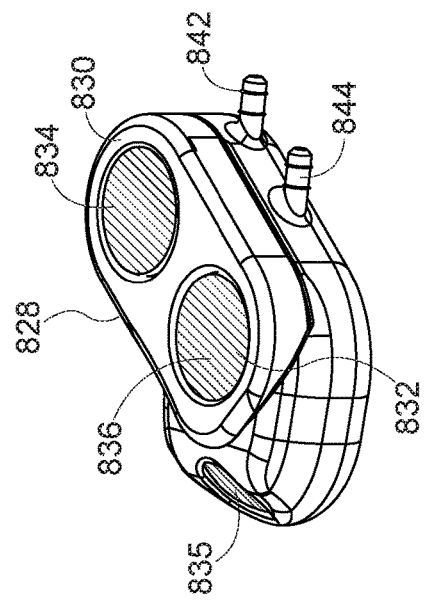
FIG. 14 is a side perspective view of the embodiment of the hub shown in FIG. 13.
Figure 16:
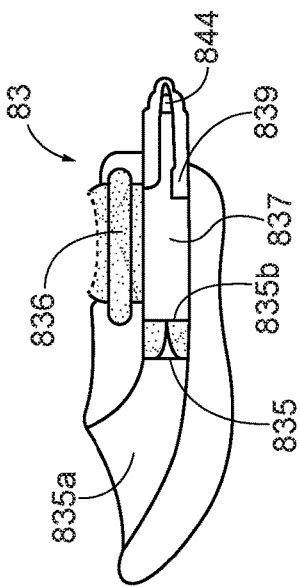
FIG. 16 is a section view across line 16-16 in FIG. 15.
Figure 13:
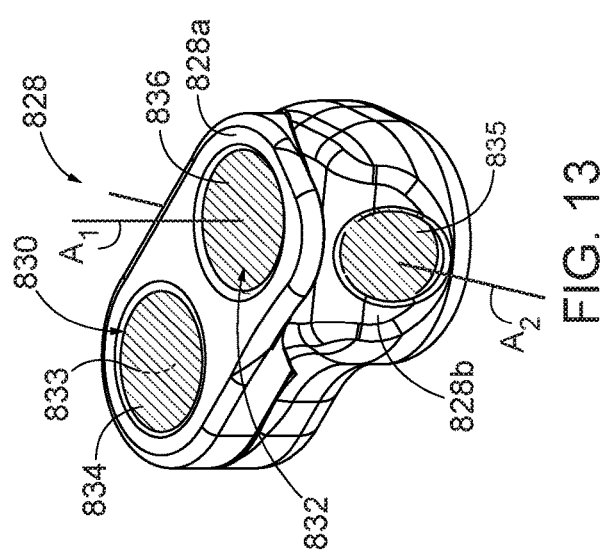
FIG. 13 is a rear perspective view of an embodiment of a hub of an implantable treatment system.
Figure 15:
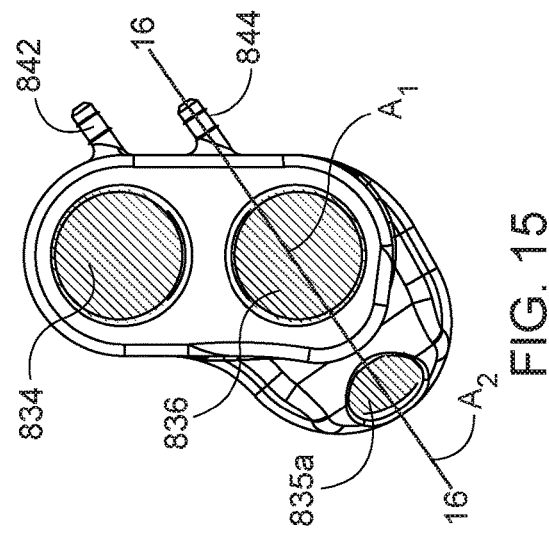
FIG. 15 is a top view of the embodiment of the hub shown in FIG. 13.
Figure 17:
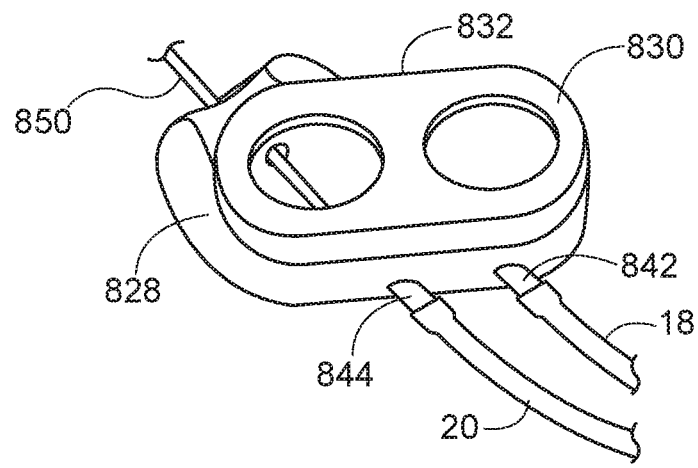
FIG. 17 is a top view of the hub shown in FIGS. 13 through 16 as part of an implantable treatment system for delivering a therapeutic treatment to a patient.

Turning now to FIG. 12, another embodiment of a treatment system 710 is shown. The treatment system 710 includes an implantable hub (not shown, but it can be similar to any of hubs 28, 128, 228, 328, 828), a first catheter 712 extending from the hub, and a second catheter 713. The second catheter 713 has a second distal opening 724 at its distal end 717. The first catheter 712 has a length between the hub and its distal opening 722 that permits the hub to be implanted at an access site, and the distal end 722 of the first catheter 712 to be located within a relatively large venous site such that it is subject to consistent systemic circulation. The second catheter 713 has a length between the hub and its distal opening 724 that permits it to be intravenously located at a selected organ, such as within the portal vein to treat the pancreas 748. As described above, pressure sensors are provided to sense systemic and localized pressures relative to the first and second distal openings 722, 724, respectively. In order to facilitate targeted radiation, a guidewire 760, provided with a series of a fiducial markers 750 along its distal end, is provided into the second catheter and in alignment with the cancerous tissue that is desired to be treated with targeted radiation. In addition, the tip of the guidewire 760 is coupled to a control wire 754 that extends back into the lumen of the second catheter 713. The control wire 754 may be incorporated into a handle or coupled to the hub. When the proximal end of the control wire 754 is actuated to pull the distal end of the guidewire 760 relative to the distal end of the second catheter 713, the distal end of the guidewire 760 changes shape in three dimensions to reposition the fiducial markers 750 in three dimensions. The dimensional information is used by the image-guided radiotherapy device to focus the treatment to the treatment site.

There have been described and illustrated herein embodiments of treatment systems and methods for therapeutic delivery. While particular embodiments of the invention have been described, it is not intended that the invention be limited thereto, as it is intended that the invention be as broad in scope as the art will allow and that the specification be read likewise. Thus, while particular embodiments include preferred dimensions for the occlusion elements in relation to particular vessels in around the pancreas, it will be appreciated that the system can be adapted, for example, in length or diameter, for a treatment provided through vessels in and around other organs, and the occlusion elements can be likewise adapted for extending completely across the relevant vessels of such other organs. Also, while the system is primarily adapted for therapeutic treatment of humans, it has been demonstrated on porcine tissues and organs, and can be used for the treatment of mammals, in general. Both humans and animals shall be considered 'patients' for purpose of this application. Further, while the systems have been described for treatment via the portal vein, the system and the pressure-responsive methods of use, may also be used to infuse treatment agents during arterial side infusions. Moreover, while various exemplar therapeutics have been disclosed, the system and methods are not limited to any specific therapeutic agent. By way of further example, and not by limitation, checkpoint inhibitors and oncolytic virus can also be used as the therapeutic agent. Also, combinations of therapeutic agents may be infused. While particular dimensions and ratios have been disclosed, it will be understood that the invention is not limited thereto. Further, while specific catheters, occluders, etc. that have been referenced with respect to the terms 'first' and 'second' in relation to the devices disclosed herein, the terms 'first' and 'second' with respect to such elements does not indicate that one is primary or more important, or require that the first be provided in order to have the second. Moreover, the terms 'first and 'second' can be used interchangeably with respect to such described components, as either catheter or occluder could have been designated as a 'first' or a 'second'. While various exemplar features of different embodiments are shown and described, it is fully within the teaching set forth herein that embodiments using various compatible and/or adaptable features described herein are within the explicit scope of the described inventions. It will therefore be appreciated by those skilled in the art that yet other modifications could be made to the provided invention without deviating from its scope as claimed.

What is claimed is:

1. A system for therapeutic delivery of a therapeutic agent in a vessel having a vessel wall, the system comprising:
   a) a subdermally implantable hub defining a first port and a second port through which respective first and second therapeutic agents can be delivered;
   b) at least one catheter defining a first lumen and a second lumen, the first lumen extending from in fluid communication with the first port to a first distal opening, and the second lumen extending from in fluid communication with the second port to a second distal opening, the second distal opening that opens at a location distally displaced from first distal opening; and
   c) a set of fiducial markers displaceable relative to the second distal opening of the second lumen, the fiducial markers adapted to be tracked by an image-guided radiotherapy system as reference points to target delivery of radiation.

2. The system of claim 1, wherein the at least one catheter comprises a first catheter defining the first lumen and a second catheter defining the second lumen.

3. The system of claim 1, wherein the at least one catheter is a single multi-lumen catheter.

4. The system of claim 1, wherein the first and second lumens run parallel to each other.

5. The system of claim 4, wherein the first and second lumens are arranged adjacent to each other.

6. The system of claim 4, wherein the first and second lumen are coaxial.

7. The system of claim 1, wherein the first and second lumen have different cross-sectional sizes.

8. The system of claim 1, wherein the first and second lumen have different cross-sectional shapes.

9. The system of claim 1, wherein the dynamic occlusion device is a filter valve including a plurality of a flexible filaments at least partially coated in a polymeric coating.

10. The system of claim 1, further comprising at least one pressure sensor adapted to sense a fluid pressure within at least one of the first and second lumens.

11. The system of claim 10, further comprising first and second pressure sensors adapted to sense fluid pressure within the first and second lumens, respectively.

12. A system for therapeutic delivery of a therapeutic agent in a vessel having a vessel wall, the system comprising:
   a) a subdermally implantable hub defining a first port and a second port through which respective first and second therapeutic agents can be delivered;
   b) at least one catheter defining a first lumen and a second lumen, the first lumen extending from in fluid communication with the first port to a first distal opening, and the second lumen extending from in fluid communication with the second port to a second distal opening, the second distal opening that opens at a location distally displaced from first distal opening;
   c) a first pressure sensor adapted to sense a first fluid pressure within the first lumen; and
   d) a second pressure sensor adapted to sense a second fluid pressure within the second lumen.

13. The system of claim 12, wherein the at least one catheter comprises first and second catheters, the first catheter defining the first lumen and the first distal opening, and the second catheter defining the second lumen and the second distal opening, each of the first and second catheters coupled to the hub.

14. The system of claim 12, wherein at least one of the first and second pressure sensors is an optical sensor.

15. The system of claim 12, further comprising a set of fiducial markers provided on or through the at least one catheter adjacent the second distal opening of the second lumen, the fiducial markers adapted to be tracked by an image-guided radiotherapy system as reference points to target delivery of radiation.

16. A system for therapeutic treatment of a patient, the system comprising:
   a) a subdermally implantable hub defining a first port and a second port through which respective first and second therapeutic agents can be delivered;
   b) at least one catheter defining a first lumen and a second lumen, the first lumen extending from in fluid communication with the first port to a first distal opening, and the second lumen extending from in fluid communication with the second port to a second distal opening, the second distal opening that opens at a location distally displaced from first distal opening; and
   c) a set of fiducial markers provided on or through the at least one catheter adjacent the second distal opening of the second lumen, the fiducial markers adapted to be tracked by an image-guided radiotherapy system as reference points to target delivery of radiation.

17. The system of claim 16, wherein the fiducial markers are linearly arranged in a spaced apart manner on the at least one catheter.

18. The system of claim 16, further comprising an actuator, wherein:
   a shapeable portion of the at least one catheter carries at least a plurality of the fiducial markers and is adapted to be re-shaped into a three-dimensional shape, and
   the actuator, upon actuation, is adapted to move the shapeable portion into the three-dimensional shape.

19. The system of claim 16, further comprising a guidewire extendable through the second lumen, wherein:
   the fiducial markers are provided to the guidewire.

20. The system of claim 19, further comprising an actuator, wherein:
   the guidewire includes a shapeable portion that carries at least a plurality of the fiducial markers and that is adapted to be re-shaped into a three-dimensional shape, and
   the actuator, upon actuation, is adapted to move the shapeable portion into the three-dimensional shape.

21. A hub for delivery of one or more therapeutic agent to a patient, comprising:
   a) a housing defining a first reservoir and a second reservoir fluidically separate from each other;
   b) a first catheter connector in fluid communication with the first reservoir;
   c) a second catheter connector in fluid communication with the second reservoir;
   d) a pierceable first septum enclosing a portion of the first reservoir and allowing access into the first reservoir via a needle;
   e) a pierceable second septum enclosing a portion of the second reservoir and allowing access into the second reservoir via a needle; and
   f) a valve within the housing and providing access to the second reservoir from a pathway excluding the second septum, the housing having a funnel-like mouth leading to the valve to guide an instrument through the valve.

22. The hub of claim 21, wherein the first and second septa are self-healing.

23. The hub of claim 21, further comprising:
a pressure sensor located in the second reservoir.

24. The hub of claim 23, further comprising:
another pressure sensor located in the first reservoir.

25. The hub of claim 21, wherein the mouth and second catheter connector are located substantially in-line with each other such that an instrument can be guided into the mouth, through the valve, into the reservoir, and out of the second catheter connector.

26. A method of delivering a therapeutic agent to a patient, comprising:
   a) providing at least one catheter having a first lumen with a first distal opening and a second lumen with a second distal opening;
   b) monitoring a local venous pressure at a first location at one of the first and second distal openings;
   c) infusing a first therapeutic agent through the first lumen and out of the first distal opening at a first flow rate; and
   d) injecting a second therapeutic agent through the second lumen and out of the second distal opening, the injecting at a significantly higher second flow rate than the first flow rate.

27. The method according to claim 26, further comprising before the infusing the first therapeutic agent, monitoring a systemic pressure of the venous system through the first lumen.

28. The method according to claim 27, wherein the infusing and the injecting are both performed through a common hub.

29. The method according to claim 28, wherein the hub includes a first port and a second port, and the infusing is via the first port, and the injecting is via the second port.

30. The method according to claim 28, wherein the hub is implanted in the patient.

31. The method according to claim 30, wherein the hub is implanted subdermally.

32. The method according to claim 26, wherein the injecting the second therapeutic agent is at a pressure at least a magnitude of order higher than the infusing.

33. The method according to claim 26, wherein the infusing and the injecting occur through separate lumens of a common catheter.

34. The method according to claim 26, wherein the infusing and the injecting occur through separate lumens of separate catheters, one of which is advanced through the other.

35. The method according to claim 26, further comprising after the injecting the second therapeutic agent, injecting a bolus of another liquid through the second port.

36. The method according to claim 26, further comprising after the injecting the second therapeutic agent, injecting a bolus of saline to through the second lumen and out of the second distal opening.

37. The method according to claim 26, wherein the first distal opening resides in the superior vena cava, and the second distal opening resides in the portal vein.

38. The method according to claim 26, further comprising preventing retrograde flow from the second distal opening toward the first distal opening.

39. The method according to claim 26, further comprising automatically and dynamically preventing retrograde flow from the second distal opening toward the first distal opening.

40. A method of delivering a therapeutic agent to a patient, comprising:
 a) inserting at least a first catheter into the patient, the at least first catheter defining first and second lumen opening to first and second distal openings, respectively;
 b) monitoring a systemic venous pressure with a first pressure sensor provided in communication with the first lumen;
 c) infusing a first therapeutic agent through a first lumen and out of the first distal opening and into the patient;
 d) monitoring a target venous pressure at a target location with a second pressure sensor provided in communication with the second lumen; and
 e) injecting a second therapeutic agent to the target location at a pressure significantly higher than the pressure of the infusing.

41. The method of claim 40, further comprising automatically preventing retrograde flow from the second distal opening toward the first distal opening.

42. The method of claim 40, wherein the first distal opening resides in the superior vena cava, and the second distal opening resides in the portal vein.

43. The method of claim 40, wherein the first and second lumen are coupled to a hub.

44. The method of claim 43, further comprising implanting the hub in the patient.

45. A method of delivering a therapeutic agent to a patient, comprising:
 a) implanting a therapeutic delivery device in the patient;
 b) first delivering a first therapeutic agent through the delivery device to a first venous location subject to systemic circulation; and
 c) second delivering a second therapeutic agent different from the first therapeutic agent through the delivery device to a second venous location subject to localized circulation.

46. The method of claim 45, wherein the second delivering is performed at a higher pressure than the first delivering.

47. The method of claim 45, wherein the first therapeutic agent is a chemotherapy agent, and the second therapeutic agent is a living cell therapy.

48. The method of claim 45, wherein the first venous location is the superior vena cava, and the second venous location is a venous outlet of an organ.

49. The method of claim 45, further comprising monitoring the pressure of the localized circulation prior to the second delivering.

50. A method of delivering a therapeutic treatment to a patient with a diseased tissue, comprising:
 a) providing at least one catheter having at least one lumen, and a hub having a port couplable to a proximal end of the at least one catheter and in communication with the at least one lumen, the at least one catheter having a distal end provided with a set of fiducial markers;
 b) inserting the distal end of the at least one catheter into a blood vessel of a patient, the blood vessel passing within close proximity of the diseased tissue;
 c) using an image-guided radiotherapy system to monitor the markers as the markers move in space; and
 d) delivering a radiotherapy dose to the diseased tissue using guidance information from the monitored markers.

51. The method of claim 50, wherein the distal end of the at least one catheter is provided with markers by having the markers directly provided to the at least one catheter.

52. The method of claim 50, wherein the providing further includes providing a guidewire with the markers thereon, and
 the distal end of the at least one catheter is provided with the markers by inserting the guidewire within or through the distal end of the at least one catheter.

53. The method of claim 50, further comprising after inserting, moving the markers from a first configuration to a three-dimensional second configuration.

54. The method of claim 50, further comprising subdermally implanting the hub in the patient.

55. The method of claim 50, further comprising delivering a therapeutic agent through the at least one lumen to a venous location subject to systemic circulation.

56. The method of claim 50, further comprising delivering a therapeutic agent through the at least one lumen to a venous location subject to localized circulation.

57. The method of claim 50, wherein the at least one catheter includes a first lumen opening to a first venous location subject to systemic circulation, and a second lumen opening to a second venous location subject to localized circulation, and further comprising:
 delivering a first therapeutic agent through the first lumen to the first venous location; and delivering a second therapeutic agent different from the first therapeutic agent through the second lumen to the second venous location.

\* \* \* \* \*